United States Patent [19]
Nuñez et al.

[11] Patent Number: 5,800,514
[45] Date of Patent: Sep. 1, 1998

[54] SHAPED WOVEN TUBULAR SOFT-TISSUE PROSTHESES AND METHODS OF MANUFACTURING

[75] Inventors: Jose F. Nuñez, Kearny, N.J.; Peter J. Schmitt, Garnerville, N.Y.

[73] Assignee: Meadox Medicals, Inc., Oakland, N.J.

[21] Appl. No.: 653,028

[22] Filed: May 24, 1996

[51] Int. Cl.⁶ .................................................. A61F 2/06
[52] U.S. Cl. .......................... 623/1; 623/11; 623/12; 623/66; 600/36; 604/8; 139/384 R; 139/387 R; 139/389; 606/155
[58] Field of Search ........................... 623/1, 11, 12, 623/66; 606/151–158, 191–200; 600/36; 604/8; 139/384 R, 387 R, 389

[56] References Cited

U.S. PATENT DOCUMENTS

| | | |
|---|---|---|
| 180,790 | 8/1876 | Reed . |
| 444,880 | 1/1891 | Erskine ........................ 139/387 R |
| 694,108 | 2/1902 | Nierhaus ...................... 139/384 R |
| 1,065,766 | 6/1913 | Aumann . |
| 1,171,249 | 2/1916 | Reynolds . |
| 1,486,272 | 3/1924 | Adams . |
| 1,753,840 | 4/1930 | Thexton, Jr. et al. . |
| 2,222,150 | 11/1940 | Moore ........................... 139/384 R |
| 2,383,767 | 8/1945 | Brownlow et al. . |
| 2,410,394 | 10/1946 | Savage . |
| 2,465,689 | 3/1949 | Lanz . |
| 2,613,693 | 10/1952 | Jarvis . |
| 2,978,787 | 4/1961 | Liebig . |
| 2,989,992 | 6/1961 | Hoyer et al. . |
| 2,998,030 | 8/1961 | Koppelman et al. . |
| 3,011,526 | 12/1961 | Nelson . |
| 3,011,527 | 12/1961 | Corbiere ....................... 139/387 R |
| 3,016,068 | 1/1962 | Felix . |
| 3,132,671 | 5/1964 | Koppelman et al. . |
| 3,156,265 | 11/1964 | Bustamante . |
| 3,258,034 | 6/1966 | Gerlach . |
| 3,316,557 | 5/1967 | Liebig ........................... 139/387 R |
| 3,347,278 | 10/1967 | Boissevain . |
| 3,426,804 | 2/1969 | Bluck . |
| 3,446,249 | 5/1969 | Wellman . |
| 3,669,157 | 6/1972 | Woodall, Jr. et al. . |
| 3,719,212 | 3/1973 | Emerson et al. ............ 139/387 R |
| 3,953,640 | 4/1976 | Takada . |
| 3,955,602 | 5/1976 | King . |
| 4,191,218 | 3/1980 | Clark et al. . |
| 4,346,741 | 8/1982 | Banos et al. . |
| 4,467,838 | 8/1984 | Rheaume . |
| 4,517,687 | 5/1985 | Liebig et al. ................ 623/1 |
| 4,530,113 | 7/1985 | Matterson ................... 623/12 |
| 4,615,256 | 10/1986 | Fukuta et al. . |
| 4,668,545 | 5/1987 | Lowe ........................... 139/387 R |
| 4,691,742 | 9/1987 | Ushiro . |
| 4,741,087 | 5/1988 | Plummer, Jr. . |
| 4,771,518 | 9/1988 | LaPointe et al. . |
| 4,777,859 | 10/1988 | Plummer, Jr. . |
| 4,816,028 | 3/1989 | Kapadia et al. ............. 623/12 |
| 4,825,912 | 5/1989 | Fleury et al. . |
| 4,848,412 | 7/1989 | Pittman et al. . |
| 4,892,539 | 1/1990 | Koch ............................ 623/1 |
| 4,923,724 | 5/1990 | Day et al. . |
| 4,949,761 | 8/1990 | Fleury et al. . |
| 5,060,350 | 10/1991 | Harris et al. . |
| 5,127,919 | 7/1992 | Ibrahim et al. ............. 623/1 |
| 5,217,769 | 6/1993 | Harris et al. . |
| 5,242,745 | 9/1993 | Aucagne et al. . |

(List continued on next page.)

FOREIGN PATENT DOCUMENTS

| | | |
|---|---|---|
| 0 698 379 A1 | 2/1996 | European Pat. Off. . |
| 3045743 | 3/1991 | Japan ........................... 139/387 R |

*Primary Examiner*—John G. Weiss
*Assistant Examiner*—Francis K. Cuddihy
*Attorney, Agent, or Firm*—Hoffmann & Baron, LLP

[57] ABSTRACT

Continuously flat-woven implantable tubular prostheses have seamless woven sections which gradually change the number of warp yarns to smoothly transition, i.e., taper, from one diameter to another. Multi-diameter endoluminal grafts having a variety of shapes and configurations are made using a seamless weaving process without unacceptable voids or gaps in the tubular wall.

33 Claims, 17 Drawing Sheets

U.S. PATENT DOCUMENTS

| | | |
|---|---|---|
| 5,246,040 | 9/1993 | Barwick et al. . |
| 5,343,897 | 9/1994 | Sakatani et al. . |
| 5,368,076 | 11/1994 | Curzio . |
| 5,370,683 | 12/1994 | Fontaine ................................... 623/1 |
| 5,381,835 | 1/1995 | Norlin . |
| 5,387,300 | 2/1995 | Kitamura . |
| 5,390,707 | 2/1995 | Cahuzac . |
| 5,394,906 | 3/1995 | Farley . |
| 5,421,372 | 6/1995 | Hsu . |

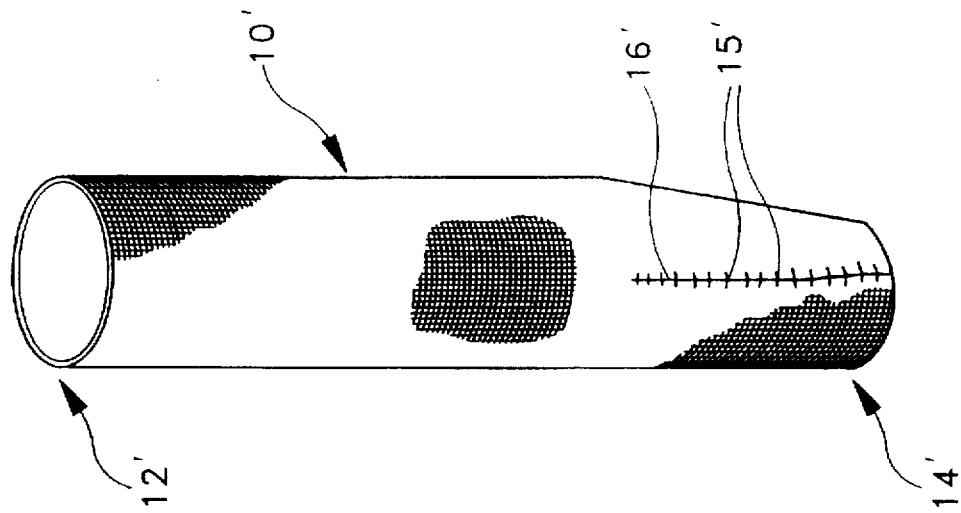
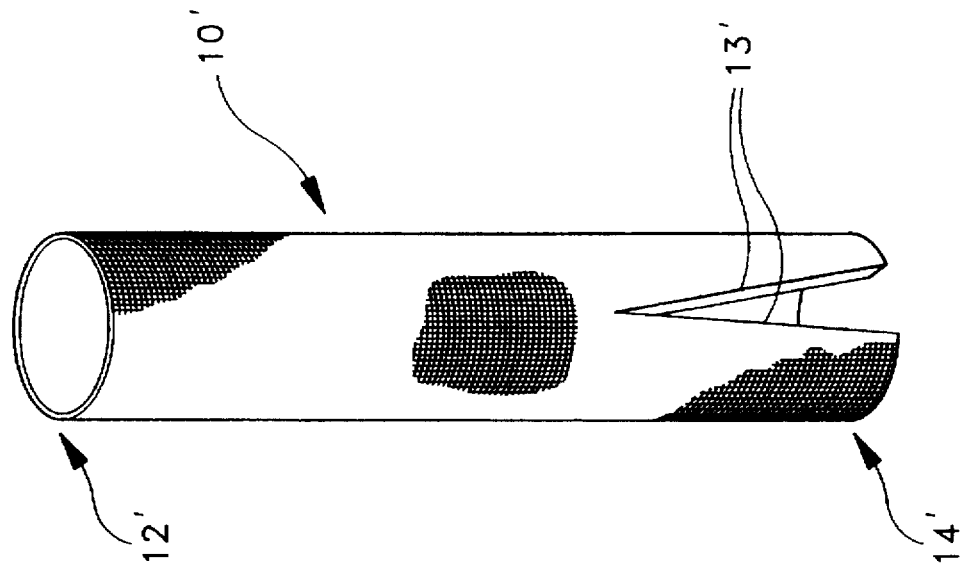
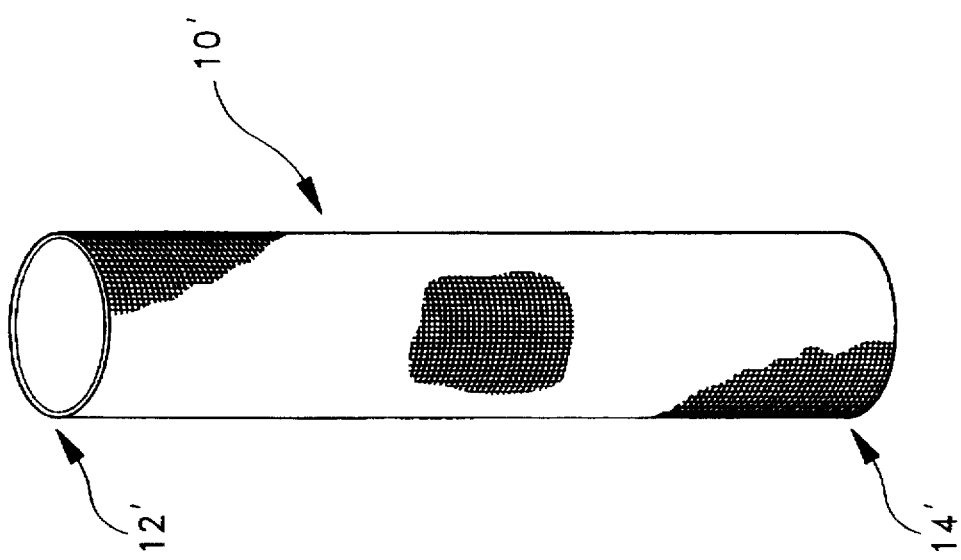

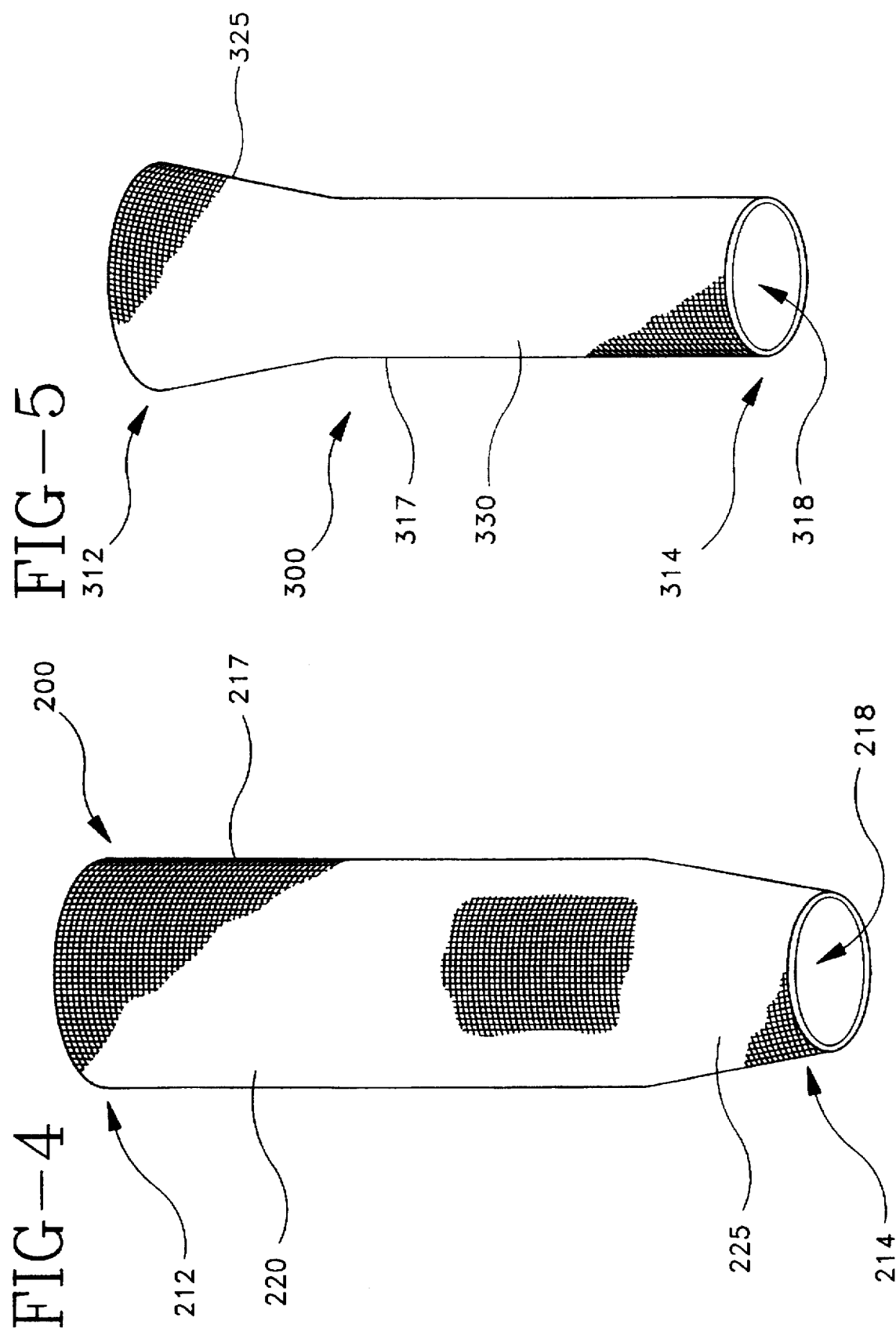

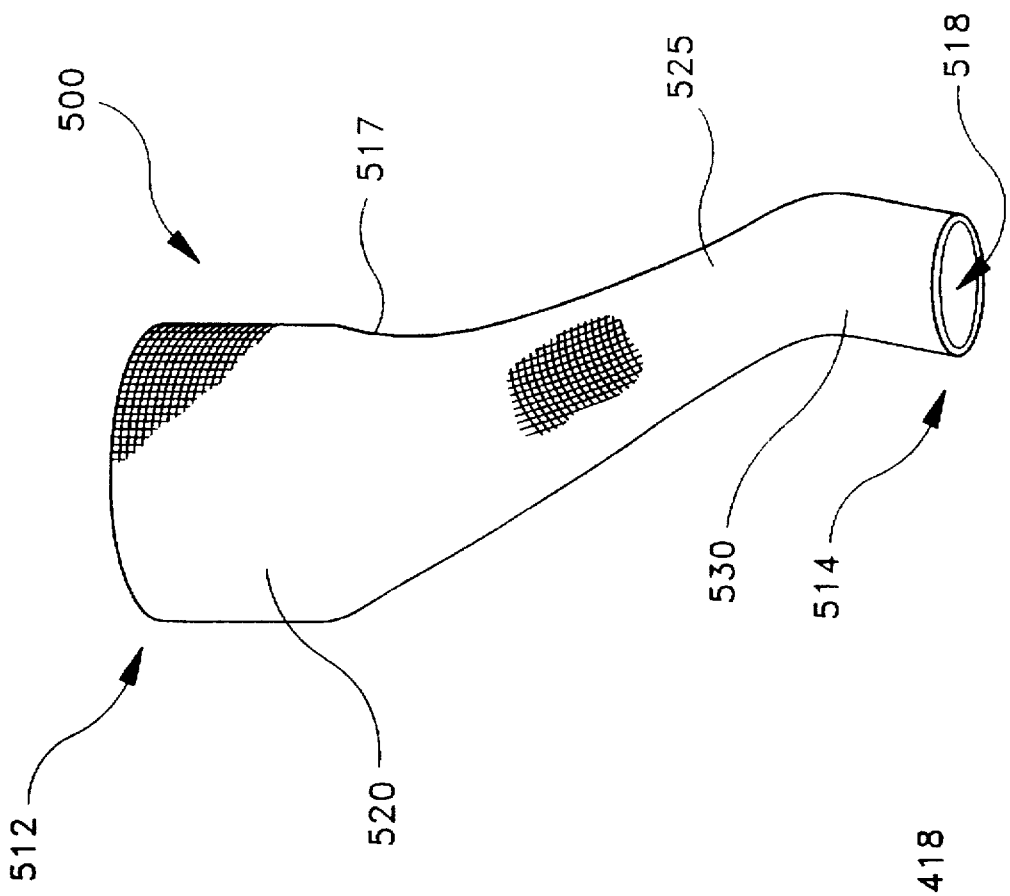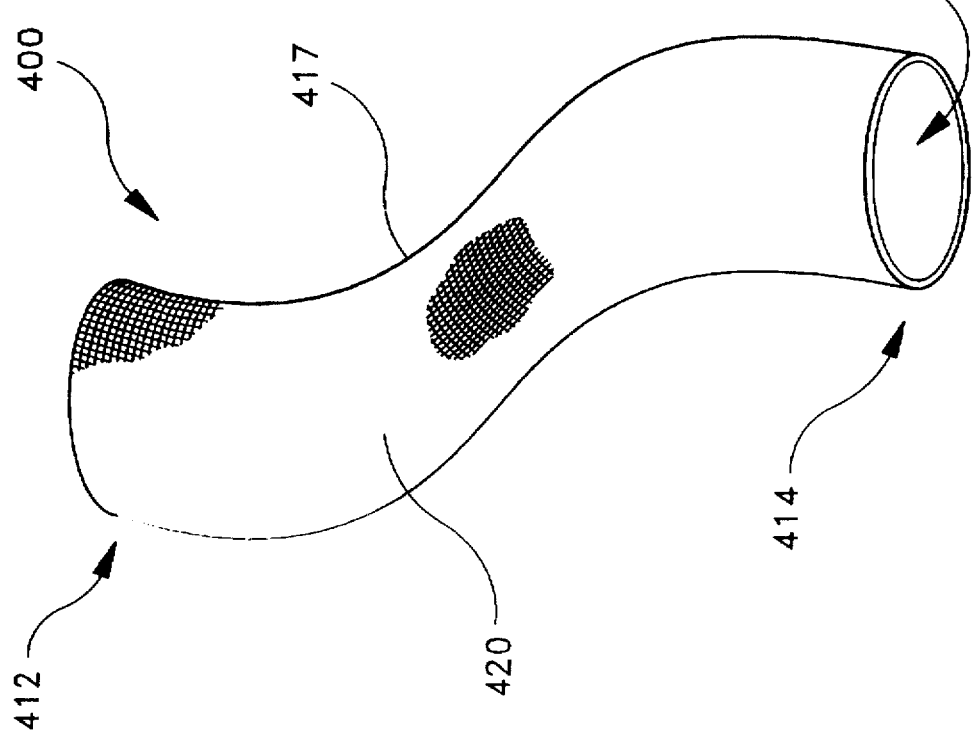

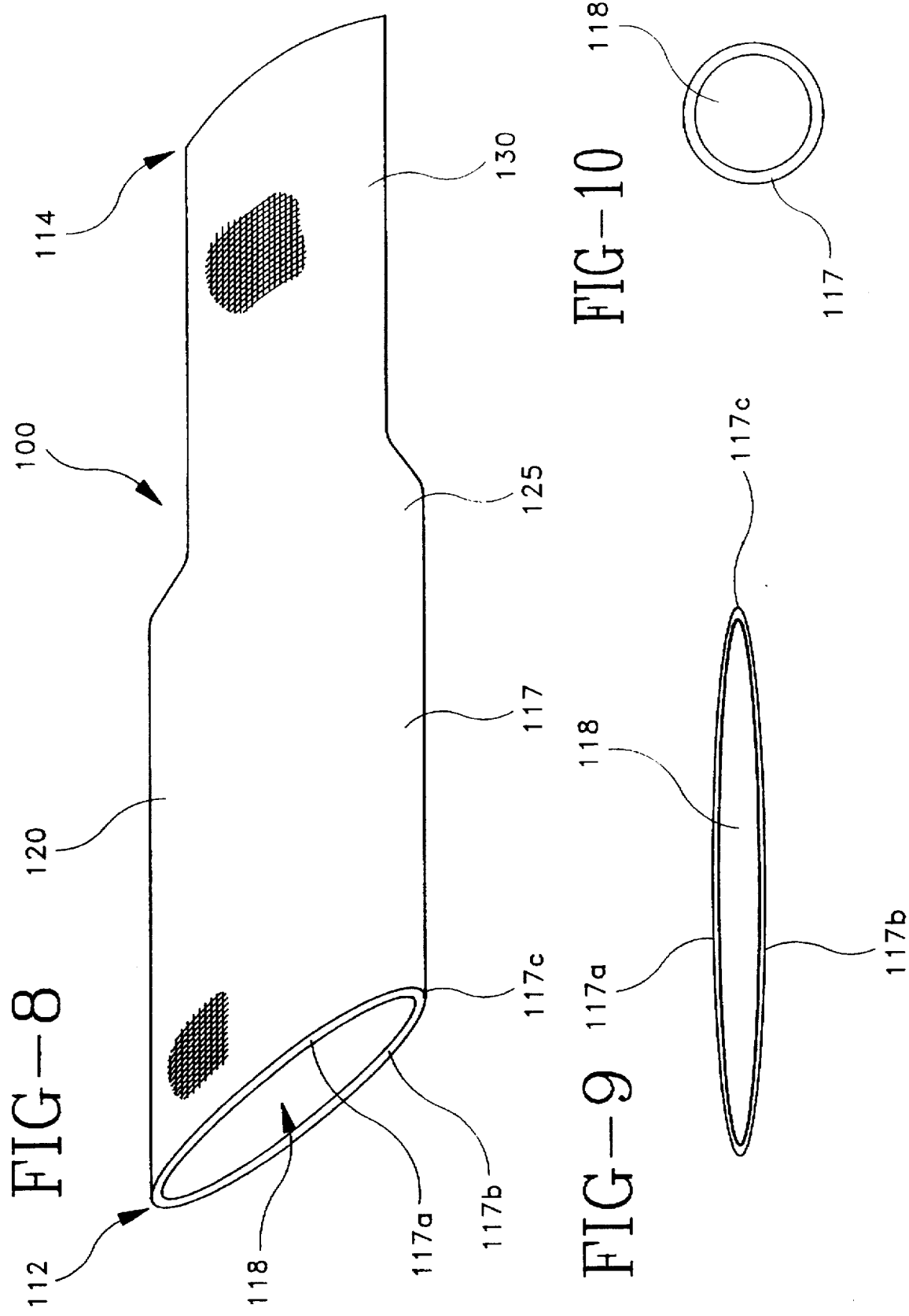

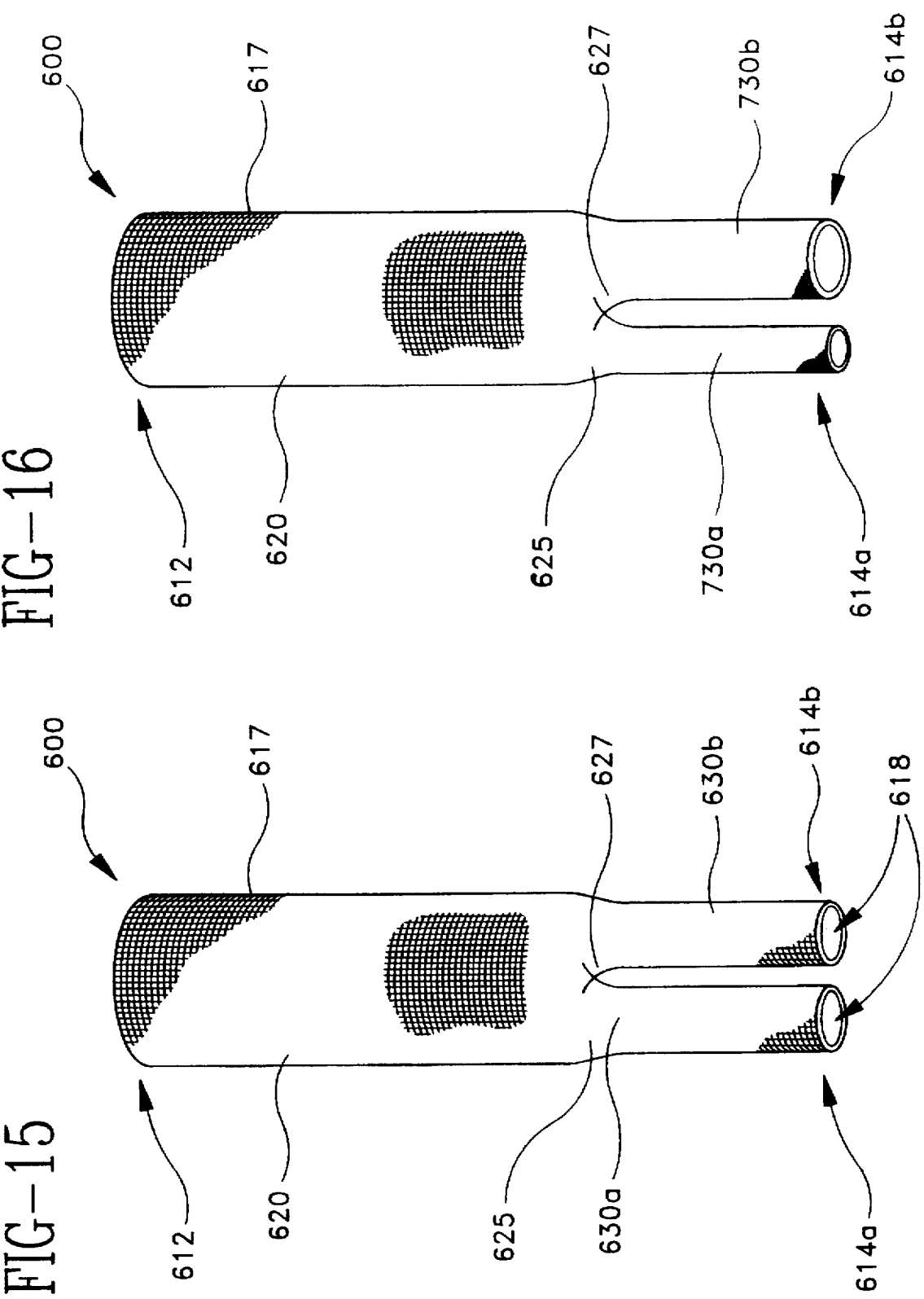

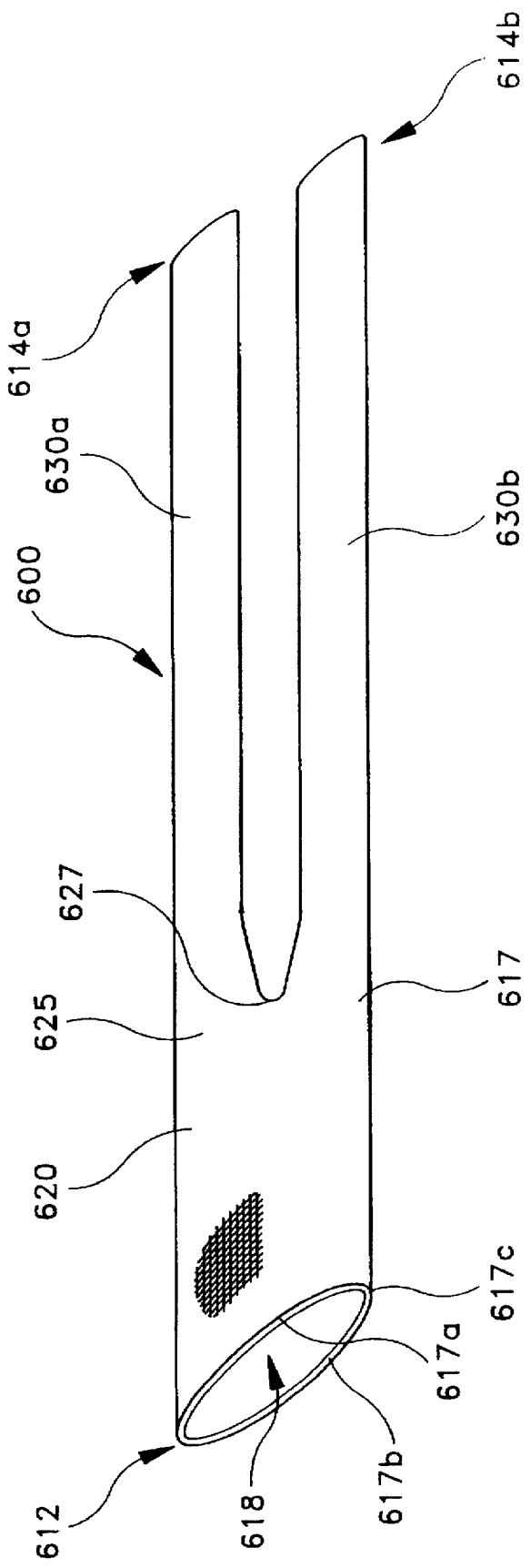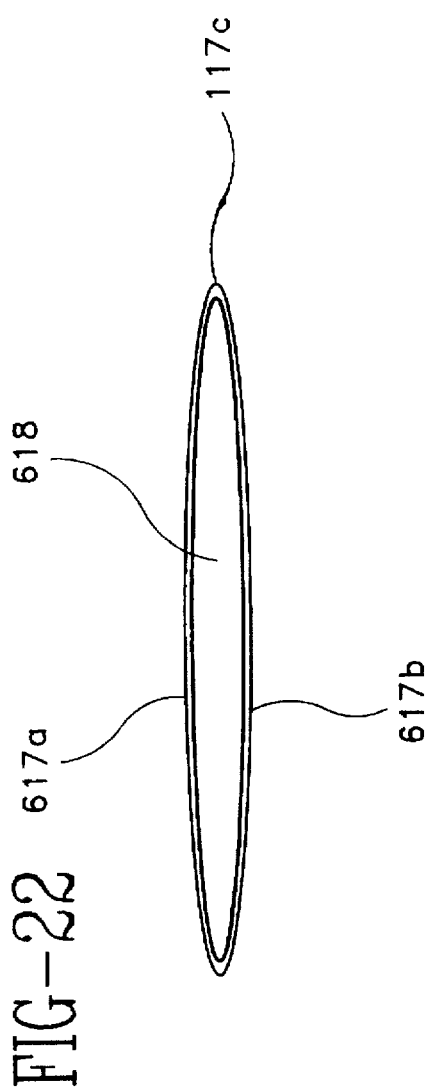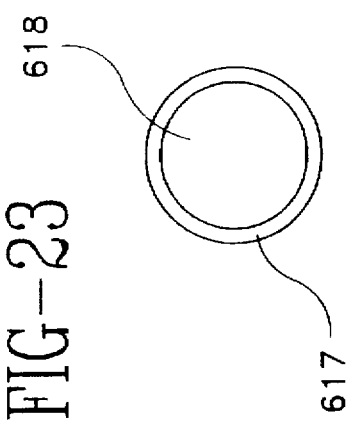

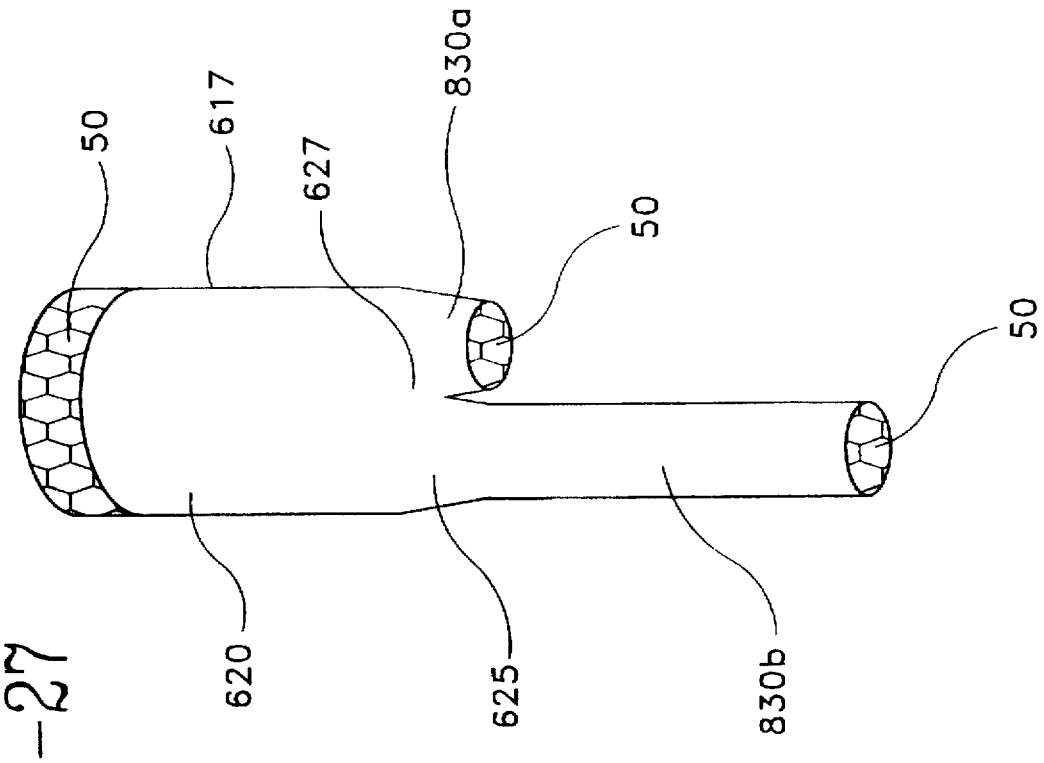
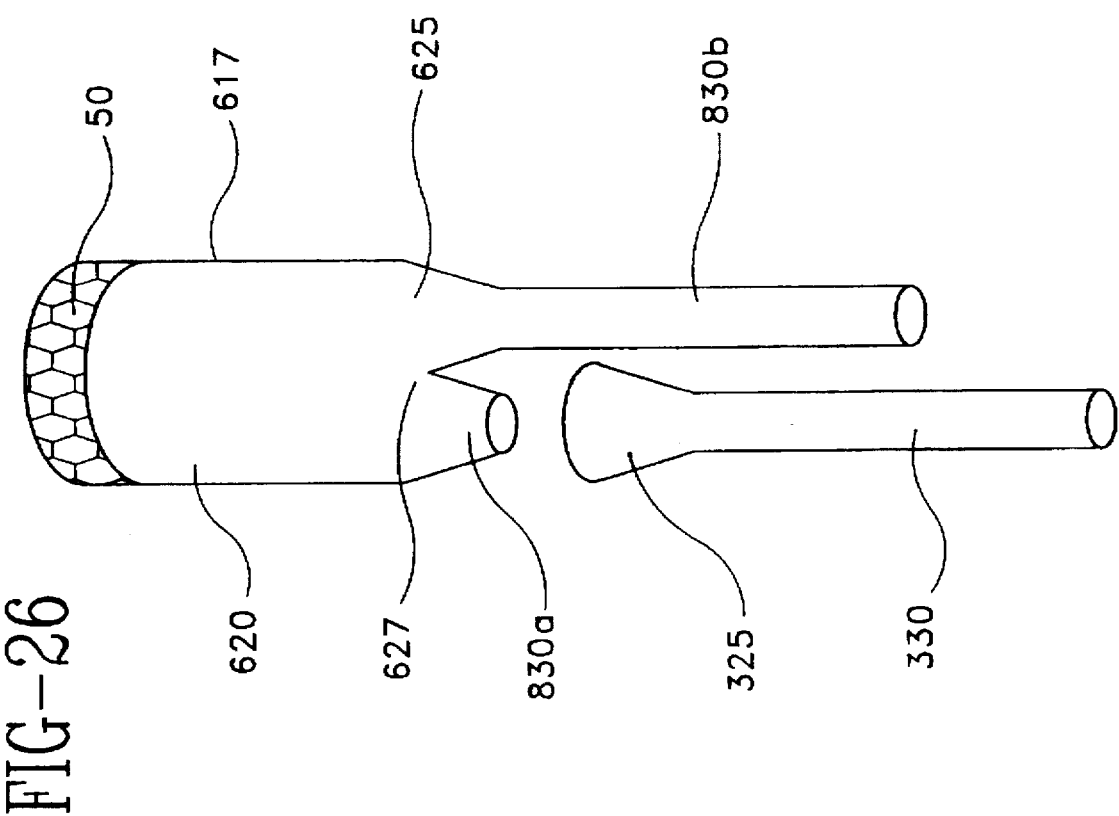

SHAPED WOVEN TUBULAR SOFT-TISSUE PROSTHESES AND METHODS OF MANUFACTURING

FIELD OF THE INVENTION

The present invention relates to shaped seamless woven tubular prostheses and methods of manufacture. In particular, the present invention relates to implantable endoluminal prostheses used in the vascular system.

BACKGROUND OF THE INVENTION

Tubular woven fabrics have been used for soft-tissue implantable prostheses to replace or repair damaged or diseased lumens in the body. In particular, endoprostheses are used in the vascular system to prevent the blood from rupturing a weakened section of the vessel. Such endoluminal conduits are generally affixed in a specified location in the vessel by means of stents, hooks or other mechanisms which serve to secure the device in place. Endoluminal tubular devices or conduits can also be used in other lumens in the body, such as in the esophagus and colon areas.

Vascular grafts have been used successfully for many years to replace segments of the diseased vessel by open surgical methods. These techniques, however, required long and expensive procedures which have a high degree of risk associated with them due to the complexity of the surgical procedures. Presently, non-invasive techniques for treating body lumens, such as vessels in the vascular system, have become more prominent because they present less risk to the patient and are less complex than open surgery. Generally, a doctor will make an incision in the femoral artery and introduce an endoluminal device by means of a catheter delivery system to the precise location of the damaged or diseased vessel. The device will generally include a stent and graft combination which is deployed from the delivery system and affixed in place usually by use of a balloon catheter. The balloon catheter is used to expand the stents which are attached to and most often contained within the graft portion. Expansion of the stent serves to both anchor the graft and to maintain the graft and the body lumen in the open state. In some cases, self-expanding stents or the like are used. Stents made from shaped-memory materials, such as nitinol, are also employed whereby radial expansion or contraction of the stent is designed to occur at specified temperatures.

The use of tubular endoluminal prostheses, however, requires a high degree of precision in the diameter of the tube, such that its external diameter matches the internal diameter of the body lumen very closely, thereby conforming to the internal surface of the body lumen. The vessels or lumens in the body, however, often vary in diameter and shape from one length to another, in addition to sometimes defining a tortuous path therebetween. This is particularly true with the vessels in the vascular system. Thus, tubular endoprostheses which are generally straight in configuration cannot accurately conform to all portions of the lumen which have these variations present. Oftentimes, the prosthesis wall will require a bunching or gathering within the lumen of the vessel which presents a long-term potential for thrombosis and generally creates a more turbulent environment for blood flow.

More recently, in recognition of certain problems in implanting and delivering endoluminal prostheses, a thinly woven graft has been made which is designed to closely fit the inner lumen of vessels. Such a graft is described in co-assigned and copending U.S. Ser. No. 08/285,334 filed on Aug. 2, 1994, herein incorporated by reference. The thinness of this graft allows for it to be easily packed into a catheter delivery system and occupy less space within the lumen when deployed. However, these grafts have been made in straight lengths or bifurcated structures using traditional weaving techniques which have specific limitations as to the final shape of the product and, in the case of bifurcated or multi-diameter grafts, the transition from one diameter to another occurs at a single point in the weave, creating a sudden change in the weaving pattern of the fabric. Such sudden changes, as further discussed herein, are considered undesirable.

Weaving is commonly employed to fabricate various tubular shaped products. For example, implantable tubular prostheses which serve as conduits, such as vascular grafts, esophageal grafts and the like, are commonly manufactured using tubular weaving techniques, wherein the tubular product is woven as a flat tube. In such weaving processes, a variety of yarns are interwoven to create the tubular fabric. For example, a set of warp yarns is used which represents the width of the product being woven, and a fill yarn is woven between the warp yarns. The fill yarn is woven along the length of the warp yarns, with each successive pass of the fill yarn across the warp yarns for each side of the tube representing one machine pick. Thus, two machine picks represent one filling pick in a tubular woven structure, since weaving one fill yarn along the entire circumference of the tube, i.e., one filling pick, requires two picks of the weaving machine. As such, in a conventional woven product, the fill yarn is woven along the length of the warp yarns for a multiple number of machine picks, with the woven product produced defined in length by the number of filling picks of the fill yarn and defined in width by the number of warp yarns in which the fill yarn is woven therebetween. Such terminology and processes are common in the art of textile weaving.

Woven tubular prostheses such as vascular grafts, having tapered diameter sections or tailored shapes such as those shown in the inventive figures discussed herein, have heretofore not been made without requiring manual customization in the form of cutting, splicing and/or tailoring with sutures. Continuous flat-weaving techniques have not been able to make diameter changes in a gradual manner, having a tapered tubular section transitioning from one diameter to another diameter. Instead, diameter changes in the woven product occur instantaneously, creating a sudden split in the warp yarns. Such a sudden split, such as at the crotch section of a bifurcated endoluminal graft, leaves gaps or voids in the weave at the splitting point. Thus, conventional bifurcated woven grafts have required sewing of the crotch section in order to insure a fluid-tight character. Such sewing is labor intensive and is generally done manually, thereby introducing the potential for human error and reliance on the technique of the technician.

Furthermore, the prior art techniques of forming tubular shapes have required manual cutting and suturing of standard woven tubes to the desired size and shape. Continuous weaving of tubular grafts to produce seamless gradual diameter transitions in devices has not been previously known. For example, the change from a first diameter to a second diameter in a single lumen, straight graft, in a continuous weaving process was not attempted due to the aforementioned limitations. Instead, individual grafts of different diameters would be individually woven and sutured together to make a continuous tube. The diameter change required customized cutting to gradually transition from one diameter to another. For example, in the case where a bifurcated graft having a 24 mm aortic section and leg sections with different diameters, e.g. 12 mm and 10 mm, the surgeon would manually cut an bifurcated graft which was formed having two equal leg sections with the same diameters, and suture a seam along that leg to form a leg of the desired different diameter. This customization required cutting and suturing. Such customization relied heavily on the skill of the physician and resulted in little quality control in the final product. Additionally, such grafts could not always be made in advance for a particular patient, since the requirements for such customization may not be known until the doctor begins the surgery or procedure of introducing the device into the body. Additionally, as previously mentioned, the suture seams take up considerable amounts of space when packed into the delivery capsule or other catheter-like device designed to deploy the endoluminal prostheses.

There is currently no prior art means to satisfy the variation in requirements from patient to patient for proper fit of the endoprosthesis. Prior art continuously woven bifurcated grafts not only suffered from the gap created at the warp yarn split, but they existed only with iliac leg portions having equal diameters. If different diameter iliac leg portions were required, this would again be accomplished through customization. One leg would be manually cut-off and another independently formed leg having a different diameter would be sutured on in its place.

Complex shapes, such as tubular "S" shaped or frustoconical shaped woven sections were not even attempted due to the impractibility, intensive labor and subsequent cost. Such shaped tubes could not practically be woven using prior art techniques.

In addition to requiring manual sewing steps, sutures used in prior art customized grafts create seams which are to be avoided in endoluminal prostheses, particularly because of the space which they take up when tightly packed into a catheter delivery system. Furthermore, such seams contribute to irregularities in the surface of the graft and potential weakened areas which are obviously not desirable.

Due to the impracticalities of manufacturing tubular grafts and endoprostheses, straight and bifurcated tubular grafts often required customization by doctors using cutting and suturing for proper size and shape.

With the present invention, designs are now possible which heretofore have not been realized. Thus, the weaving of gradually shaped tubular grafts in a continuous process to create seamless and void-free conduits for implantation in the body has heretofore not been possible. The present invention provides a process of producing such grafts, as well as providing the weaving structure inherent in products formed therefrom.

SUMMARY OF THE INVENTION

The present invention relates to flat-woven implantable tubular prostheses, and in particular endoluminal grafts, which have been continuously woven to form seamless tubular products having gradual changes in diameter along their length, as well as various shaped tubular sections formed from gradual changes in the number of warp yarns engaged or disengaged with the fill yarns during the weaving process. Changes in diameter and/or shape are accomplished by gradually engaging and/or disengaging selected warp yarns with the fill yarns in the weave pattern. It has been discovered that such a gradual transition can be accomplished using electronic jacquard looms controlled by computer software. Such engaging and/or disengaging of warp yarns can change the diameter of the tube in a manner which creates a seamless and gradual transition from one diameter to another. Additionally, such engagement and/or disengagement can be used to create tubular vascular prostheses and the like which have any number of shapes as depicted and further described herein.

Thus, in one embodiment of the present invention there is provided, a flat-woven implantable tubular prosthesis having warp yarns and fill yarns including first and second spaced apart portions which define therebetween a transition tubular wall extent, the first portion having a first diameter and the second portion having at least a second diameter different from the first diameter. The tubular prosthesis further includes a weaving pattern along the transition tubular wall extent, said weaving pattern having a gradual change in the number of warp yarns to provide a seamless transition between the first and second portions.

In another embodiment of the present invention there is provided, a flat-woven implantable tubular prosthesis including first and second ends defining a tubular wall therebetween, with the tubular wall including warp yarns and fill yarns. The tubular wall is defined by a first elongate woven section with a first selected number of warp yarns therealong to define a first tubular internal diameter, and a second elongate woven section seamlessly contiguous with the first woven section and having a gradual change in the number of warp yarns therealong to define at least a second tubular internal diameter.

In an alternative embodiment of the present invention, there is provided, a flat-woven tubular implantable prosthesis having warp yarns and fill yarns including first and second ends defining a tubular wall therebetween, with the tubular wall having a first woven extent with a first selected number of warp yarns therealong to define a first tubular internal diameter, a transitional second woven extent contiguous with the first woven section with at least a second selected number of warp yarns therealong to define at least a second tubular internal diameter which is different from the first tubular internal diameter, and at least a third woven extent contiguous with the second woven extent with a third selected number of warp yarns which is different from the first and said second selected number of warp yarns, with the third woven extent defining a third tubular internal diameter which is different from the first and second tubular internal diameters.

Additionally, methods of forming such endoluminal prostheses are also provided. In one of such methods, there is provided a method of forming a seamless flat-woven implantable tubular prosthesis including the steps of weaving a tubular wall having transitional diameter along a longitudinal extent thereof, such weaving including gradually engaging or disengaging additional warp yarns along the extent to transition from a first diameter to a second diameter different from the first diameter.

Another embodiment of the methods of the present invention includes a method of making a seamless flat-woven implantable tubular prosthesis including weaving a first section of the prosthesis having a first diameter using a first selected number of warp yarns, and transitioning to a second section of the prosthesis having a second diameter different from the first diameter by gradually engaging or disengaging warp yarns.

Additionally included in the present invention is a method of forming a flat-woven synthetic tubular implantable prostheses having a precise predetermined internal diameter (D) including the steps of: (i) choosing a desired weave pattern; (ii) providing a desired yarn and yarn size for the weaving pattern; (iii) providing a desired density (ρ) at which the yarn is to be woven; (iv) providing a number of warp yarns (S) required to weave a suitable tubing edge; (v) choosing a desired internal diameter (D) of the tubular prosthesis; (vi) calculating the total number of warp yarns (N) required to weave the tubular prosthesis having the internal diameter (D) using the formula:

$$N=S+(D\times\rho)$$

wherein N represents the total number of warp yarns required, S represents the number of warp yarns required to weave a suitable tubing edge, D represents the desired internal diameter and ρ represents the number of warp yarns per unit of diameter.

BRIEF DESCRIPTION OF THE DRAWINGS

FIGS. 1a, 1b and 1c depict perspective views of a graft constructed in accordance with the prior art.

FIGS. 2, 3, 4, 5, 6 and 7 depict perspective views of shaped grafts constructed in accordance with various embodiments of the present invention.

FIG. 8 is a perspective view of a graft of the present invention having a first diameter tapering to a second diameter shown in a flat, radially compressed form after weaving but prior to heat setting.

FIG. 9 is a cross-sectional view of the graft shown in FIG. 8.

FIG. 10 is a cross-sectional view of the graft of FIG. 8 after heat setting.

FIGS. 15, 16 and 17 depict perspective views of bifurcated grafts constructed in accordance with alternative embodiments of the present invention.

FIG. 21 is a perspective view of a bifurcated graft of the present invention shown in a flat, radially compressed form after weaving, but prior to heat-setting.

FIG. 22 is a cross-sectional view of the graft shown in FIG. 21.

FIG. 23 is a cross-sectional view of the graft of FIG. 21 after heat setting.

FIG. 26 is a perspective view of the bifurcated graft of FIG. 17 used in connection with the tapered graft of FIG. 5, with an internal stent shown at one portion of the graft.

FIG. 27 is a perspective view of the bifurcated graft of FIG. 17 including an internal stent extending therethrough.

DETAILED DESCRIPTION OF THE PREFERRED EMBODIMENT

Figure 2:
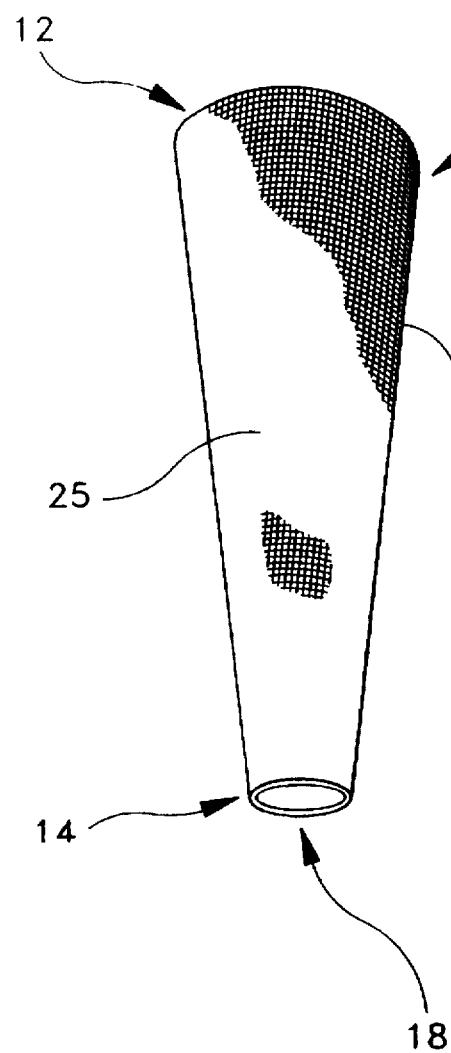

It has been discovered through the present invention that tubular woven textile products such as vascular grafts can be seamlessly woven into a variety of shapes and sizes, without the need for any post-weaving fabrication techniques such as cutting, sewing, suturing and the like.

A recurrent problem and limitation in prior art techniques of tubular weaving can be evidenced through the prior art techniques for manufacturing split grafts, such as bifurcated grafts, trifurcated grafts, and the like. A split graft consists of a tubular graft section of a certain diameter, which splits at a crotch area into a plurality of tubular graft sections or members of a different diameter than the first graft section. For example, a bifurcated graft, as depicted in FIG. 15, includes an aortic woven portion 620 with a crotch 627, and splits into first and second iliac woven portions 630a and 630b. For the purposes of the present invention, split grafts are designated as having a first graft section referred to as an aortic woven portion and second graft sections referred to as iliac woven portions or iliac leg sections, since in preferred embodiments, such split grafts, i.e. bifurcated grafts, are meant for implantation within the aorta at the branch of the iliac arteries, for instance, for use in repairing an aortic aneurism.

In conventional manufacturing processes for tubular weaving of bifurcated grafts, it was necessary to split the number of warp yarns at the crotch area during the weaving process in order to split the tubular woven graft from the first aortic woven portion 620 into the first and second iliac woven portions 630a and 630b. This splitting of warp yarns was necessary in order to accomplish the transition at the crotch 627, where the diameter of the graft transitions from a first inner diameter of the aortic woven portion 620 to two separate inner diameters representing the first and second iliac woven portions 630a and 630b. In prior art processes, however, such transition in split grafts from a first diameter to two equal second diameters was accomplished by splitting the warp yarns evenly at the crotch 627 during the weaving process. It is known that it is desired to us an odd number of warp yarns in order to form a continuous plain weave pattern for tubular weaving. Thus, such splitting of the number of warp yarns in half at the crotch area in order to form iliac leg portions in prior art processes resulted in an incorrect number of warp yarns in one of the iliac leg portions, since the number of warp yarns required in the tubular weaving of the aortic portion was of an odd number, and splitting this odd number in half results in an odd number and an even number. Thus, in prior art processes, at least one of the iliac leg portions of a tubular woven graft often included an incorrect weave pattern at the flat-woven edge.

In an effort to correct this problem resulting in the wrong number of warp yarns in one of the iliac leg portions, the present inventors discovered that it is possible to disengage a warp yarn from the weave pattern for that portion of the weaving process required to weave the iliac leg portions without deleterious effects. In the prior art weaving processes the number of warp yarns generally remained constant throughout the weaving pattern, due to the inefficiencies and impracticability of disengaging a warp yarn for only a portion of the weaving pattern. The present invention utilizes specially designed software and a customized electronic tubular weaving machine for disengaging a warp yarn for a portion or portions of the weaving pattern. Thus, by disengaging one warp yarn from the weave pattern at the crotch area during the weaving process, an odd number of warp yarns could be utilized during the weaving of the iliac leg sections of the graft, and the correct weave pattern would be produced throughout the entire graft.

As previously discussed, a further problem with prior art processes in the manufacture of tubular woven grafts related to achieving precise diameters of the graft. Oftentimes, the portion of a damaged blood vessel to be repaired included a taper or diameter change, wherein the blood vessel changes from one diameter to a second diameter over the area to be repaired. In the prior art, in order to compensate for such changes in diameters, a surgeon commonly cuts a seamless tubular woven graft along its length, as demonstrated in FIG. 1a, 1b and 1c. In FIG. 1a, a seamless tubular woven graft 10' is depicted, having a first end 12' and a second end 14', with an internal diameter extending through the tubular graft. As shown in FIG. 1b, a cut in the wall of the graft was made, leaving cut edges 13'. Thereafter, the cut edges 13' were sutured together by a surgeon with edge sutures 15', thereby providing a tubular woven graft 10' with one diameter at first end 12' which gradually tapers to a second diameter at second end 14' by way of taper seam 16'. Such a tapering process, however, involved a post-fabrication technique, resulting in a tubular woven graft which was no longer seamless and required additional steps after fabrication of the graft.

In order to overcome these problems, the present inventor discovered that such a tubular-woven graft could be tapered during the weaving process, producing a seamless tubular-woven graft having a tapered configuration, as well as a variety of other tapers, flares, and shapes as shown in FIGS. 2 through 7.

With reference to FIG. 2, a typical seamless tubular-woven textile graft 10 in accordance with the present invention is shown generally as a tapered graft in a generally frustoconical shape. Graft 10 is a textile product formed of a woven synthetic fabric. Graft 10 is depicted in one embodiment in FIG. 2 which includes a generally tubular body 17 having a first end 12 and an opposed second end 14, defining therebetween an inner lumen 18 which permits passage of blood once graft 10 is implanted in the body. Graft 10 includes continuous transitional woven portion 25 extending between first end 12 and second end 14, and extending along the entire length of graft 10. Graft 10 of FIG. 2 has a generally frustoconical shape, with first end 12 having a first tubular inner diameter and second end 14 having a second tubular inner diameter which is different than the inner diameter of first end 12. For example, first end 12 may have an inner diameter of 12 millimeters and second end 14 may have an inner diameter of 10 millimeters, with transitional woven portion 25 forming a gradual taper having successive changes in diameter throughout such that graft 10 gradually tapers from the 12 millimeter inner diameter of first end 12 to the 10 millimeter inner diameter of second end 14 along the length of transitional woven portion 25. The gradual tapering of transitional woven portion 25 is accomplished by gradually disengaging and/or engaging a selected number of warp yarns from the weaving pattern during weaving of the graft, as will be discussed in more detail herein.

Figure 3:
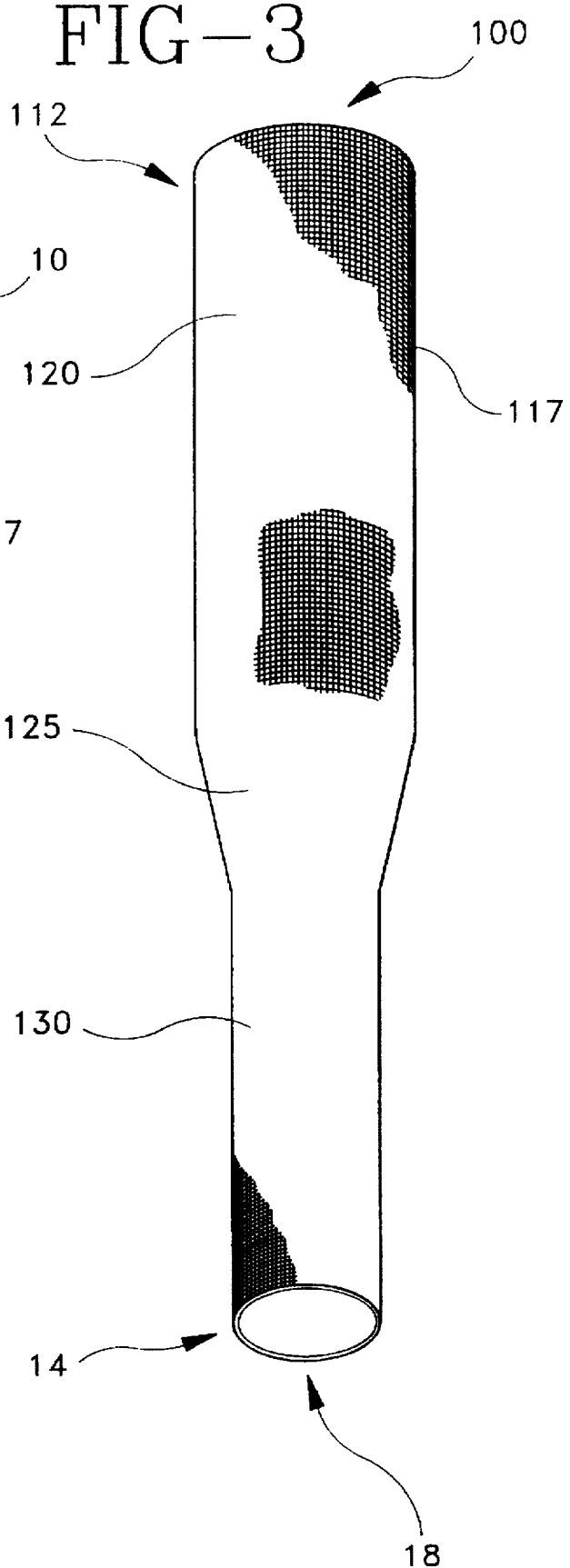

FIGS. 3, 4, 5, 6 and 7 show various shapes of grafts that can be formed according to the present invention. FIG. 3 shows a variation of the configuration of FIG. 2, with graft 100 in the form of a step-tapered graft having a tubular body 117 with a first end 112 and an opposed second end 114 defining an inner lumen 118 therebetween. In the embodiment of FIG. 3, graft 100 includes first woven portion 120 which defines a portion of tubular wall 117 having a continuous first inner diameter and second woven portion 130 which defines a portion of tubular wall 117 having a continuous second inner diameter which is different than the inner diameter of first woven portion 120. Graft 100 of FIG. 3 further includes transitional woven portion 125 adjacent and contiguous with first and second woven portions 120 and 130. In such an embodiment, graft 100 includes a constant diameter extending through first woven portion 120 and a constant diameter which is different than the inner diameter of first woven portion 120 which extends through second woven portion 130, and gradually tapers from the inner diameter of first woven portion 120 to the inner diameter of second woven portion 130 through the length of transitional woven portion 125.

FIG. 4 shows a further variation on the step-tapered configuration of FIG. 3, with graft 200 having a tubular body 217 with a first end 212 and an opposed second end 214 defining an inner lumen 218 therebetween. In the embodiment of FIG. 4, graft 200 includes a first woven portion 220 and a transitional woven portion 225, with the first woven portion 220 defining first end 212 and including a continuous inner diameter along the length thereof, and the transitional woven portion 225 defining second end 214 and including a gradual taper such that graft 200 gradually tapers from the inner diameter of first woven portion 220 to a second diameter at second end 214 which is different than the inner diameter of first woven portion 220. It is contemplated that such gradual tapering can be either an inward taper or an outward taper (flared).

FIG. 5 shows a further variation on the configuration of graft 10 of FIG. 2, with graft 300 having a tubular body 317 with a first end 312 and an opposed second end 314 defining an inner lumen 318 therebetween. In the embodiment of FIG. 5, graft 300 includes a transitional woven portion 325 and a second woven portion 330, with the transitional woven portion 325 defining first end 312 and the second woven portion 330 including a continuous inner diameter along the length thereof, and defining second end 314. Further, transitional woven portion 325 includes a gradual taper such that graft 300 gradually tapers outwardly from the inner diameter of first end 312 to a second diameter at second end 314 which is different than the inner diameter of first end 312.

FIGS. 6 and 7 show further shapes which can be formed according to the present invention. FIG. 6 depicts a sinusoidal shaped graft 400 having a tubular body 417 with a first end 412 and an opposed second end 414 defining an inner lumen 418 therebetween. In the embodiment of FIG. 6, graft 400 includes a continuous first woven portion 420, with the first woven portion 420 defining both first and second ends 412 and 414. First woven portion 420 has a continuous inner diameter along the length thereof, such that first end 412 and second end 414 have the same inner diameter. Graft 400 is shaped along its length in an "S" configuration, with tubular body 417 gradually changing direction as warp yarns on one edge of graft 400 during the weaving process are engaged or disengaged while the same portion of tubular body 417 on the other edge of graft 400 equally changes in the same direction as warp yarns are engaged or disengaged at this edge. Thus, as warp yarns at one edge of the graft are disengaged as that edge and shape of the graft gradually curves, the corresponding warp yarns at the opposite edge on the same pick are engaged. As the "S" shape again changes direction, the opposite may be true, i.e., warp yarns at a given pick on one edge may be engaging as corresponding warp yarns at the other edge on the same pick may be disengaging. In order to maintain a constant diameter, the warp yarns at each of the edges of the tubular graft must simultaneously change by additionally adding or engaging an equal number of warp yarns on one edge as the other edge loses or disengages warps. Thus, the total number of warp yarns within the tubular wall remains constant during the weaving process.

FIG. 7 depicts a variation of the sinusoidal shaped graft 400 shown in FIG. 6. Graft 500 in FIG. 7 includes a tubular body 517 with a first end 512 and an opposed second end 514 defining an inner lumen 518 therebetween. In the embodiment of FIG. 7, graft 500 includes first woven portion 520 having a first inner diameter and second woven portion 530 having a second inner diameter which is different than the inner diameter of first woven portion 520. Graft 500 further includes transitional woven portion 525 adjacent first and second woven portions 520 and 530. For example, first woven portion 520 may include a woven graft section having an inner diameter of 12 millimeters and second woven portion 530 may include a woven graft section having an inner diameter of 10 millimeters, with transitional woven portion 525 forming a gradual taper such that graft 500 gradually tapers from the 12 millimeter inner diameter of first woven portion 520 to the 10 millimeter inner diameter of second woven portion 530 along the length of transitional woven portion 525. Graft 500 is shaped along its length in an "S" configuration similar to the manner in FIG. 6, with tubular body 517 gradually tapering in on one side of graft 500 during the weaving process while the same portion of tubular body 517 on the other side of graft 500 tapers outwardly.

While a variety of shapes and configurations are shown in the drawings and described herein, any seamless tubular flat-woven graft incorporating a gradual transitional continuously woven portion is contemplated by the present invention. The gradual tapering of the transitional woven portion is accomplished in each of the inventive embodiments by gradually disengaging and/or engaging a selected number of warp yarns from the weaving pattern during weaving of the graft, as will be discussed in more detail herein.

Through the present invention it is now possible to accomplish disengaging and/or engaging of selected warp yarns to create gradual changes with size, shape or configuration of the graft during weaving of the graft. It has been discovered through the present invention, however, that such disengaging and/or engaging of the warp yarns must be accomplished in a gradual transition in order to prevent holes or voids between the contiguous sections of the woven graft. It is known that a delicate balance exists between porosity of the graft for proper ingrowth and the need in many applications for fluid-tight walls. It has been determined that a void greater than the diameter of about three warp yarns results in a graft with a porosity which is unacceptable as a fluid-tight conduit and may be incapable of sufficiently maintaining blood pressure therein. Thus, the transition from a graft section of one diameter to a graft section of another diameter must be accomplished in fluid-tight applications without creating such voids between the contiguous weave sections which are generally greater than the diameter of three warp yarns. In applications where fluid-tight walls are not crucial, the size of such voids may of course be greater.

Any type of textile product can be used as the warp yarns and fill yarns of the present invention. Of particular usefulness in forming the woven prostheses of the present invention are synthetic materials such as thermoplastic polymers. Thermoplastic yarns suitable for use in the present invention include, but are not limited to, polyesters, polypropylenes, polyethylenes, polyurethanes and polytetrafluoroethylenes. The yarns may be of the monofilament, multifilament, or spun type.

The yarns used in forming the woven grafts of the present invention may be flat, twisted or textured, and may have high, low or moderate shrinkage properties. Additionally, the yarn type and yarn denier can be selected to meet specific properties desired for the prosthesis, such as porosity, flexibility and compliance. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 1000, preferably from about 40 to about 300. Preferably, the warp and fill yarns are polyester, and most preferably the warp and fill yarns are one ply, 50 denier, 48 filament flat polyester.

The graft of the present invention can be woven using any known weave pattern in the art, including, simple weaves, basket weaves, twill weaves, velour weaves and the like, and is preferably woven using a flat plain tubular weave pattern, most preferably with about 170–190 warp yarns (ends) per inch per layer and about 86–90 fill yarns (picks) per inch per layer. The wall thickness of the graft may be any conventional useful thickness, but is preferably no greater than about 0.16 mm, with the most preferable wall thickness being from about 0.07 mm to about 0.14 mm. These thicknesses facilitate the folding of the graft into an appropriate delivery system. Moreover, the seamless (i.e., sutureless) feature of the present invention further facilitates packing and folding of the graft into the delivery system.

As noted, transition from one diameter to another diameter is accomplished by gradually engaging and/or disengaging selected warp yarns from the weave pattern. In the present invention, it has been discovered that such a transition can be effectively accomplished by engaging or disengaging a maximum of three warp yarns per four successive machine picks for a given weave pattern on each edge of the graft. Such disengaging or engaging of warp yarns can be accomplished in any combination of numbers. For example, up to three warp yarns can be disengaged or engaged at any of the four successive machine picks, as long as the total number of warp yarns engaged and/or disengaged does not exceed a maximum of three warp yarns per four machine picks on each edge of the tubular flat-woven product. An edge is defined as an outer limit of the graft width as taken along the longitudinal axis as the graft is flat-woven on the loom. FIG. 8 shows such edges at 117c. As previously noted, two machine picks represents one filling pick of tubular fabric, i.e., one tubular fill yarn. Thus, four machine picks represents two tubular fill yarns.

As noted above, preferably the tubular-woven graft of the present invention is constructed of polyester which is capable of shrinking during a heat set process. For instance, such grafts are typically flat-woven in a tubular form. Due to the nature of the flat-weaving process, the tubular graft is generally flat in shape after weaving, as depicted in FIG. 8, which shows a graft 100 in one embodiment of the present invention as flat-woven in a tubular step-tapered form as shown in FIG. 3. As shown in cross-sectional view in FIG. 9, such a flat-woven tubular graft subsequent to weaving is generally eliptical. Such grafts, however, when constructed of heat-settable polyester yarn, can be heat set on a mandrel to form a generally circular shape, as depicted in FIG. 10.

Such a heat setting process is accomplished by first flat-weaving the graft in a tubular form out of a material capable of shrinking during a heat setting process. After the graft is woven, the graft is placed on a mandrel, and heated in an oven at a temperature and time capable of causing the yarns of the graft to heat set to the shape and diameter of the mandrel. Preferably polyester yarns are used as the warp and fill yarns, and the heat setting is accomplished at time and temperatures appropriate for the material. For example, heat setting can be accomplished at about 190°–200° C. for a period of about 14–16 minutes. Other methods of heat setting known in the art may be employed. After such a heat setting process, the graft can be formed into a shape desired for implantation, having a generally circular inner lumen.

As noted above, due to the nature of the flat-weaving process, while graft 100 is tubular, it is generally flat in shape during weaving and prior to the aforementioned heat setting, as shown in FIG. 9. The post-fabrication flat shape of tubular wall 117 is comprised of top tubular body portion 117a and bottom tubular body portion 117b, which connect at tubular body edges 117c. While reference has been made to a heat setting process for forming graft 100 into a generally cylindrical shape as shown in FIG. 10, graft 100 can be provided as a finished product in the generally flat shape shown in FIG. 9, or can be made cylindrical in shape by any known methods. Further, crimping of the graft 100 along the length of tubular wall 117 to provide structural integrity is contemplated.

Figure 11A:
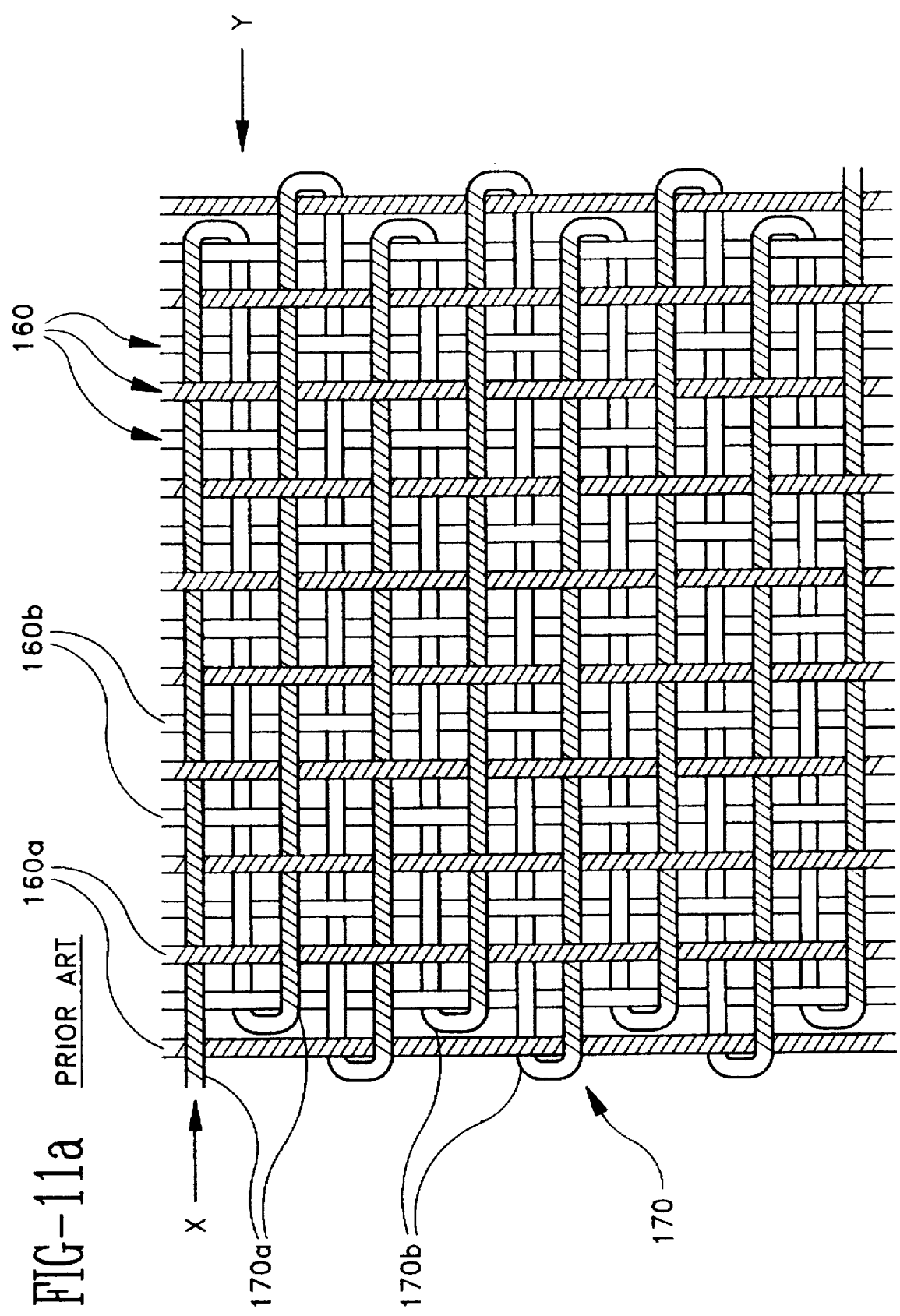
FIGS. 11a and 11b are perspective views of weave patterns in accordance with the present invention.

FIG. 11a shows a conventional plain tubular weave pattern known in the art. Warp yarns 160 are further shown as 160a indicating they are in the top layer of the weave and 160b indicating their presence in the bottom layer of the weave. Top warp yarns 160a and bottom warp yarns 160b run in a lengthwise direction in the graft and define the width of the graft. Fill yarns 170 are further shown as top fill yarns 170a and bottom fill yarns 170b. These fill yarns are woven with the top and bottom warp yarns 160a and 160b as shown in FIG. 11a in a manner known in the art. For example, a filling yarn shuttle (not shown) passes across warp yarns 160 while selected warp yarns 160 are lifted according to a specific weave pattern. In electronic weaving machines, such weave patterns can be programmed using software into the machine. In a typical plain tubular weave as depicted in FIG. 11a, the shuttle first weaves top fill yarn 170a by passing across warp yarns 160 while certain warp yarns 160 are lifted. During travel of top fill yarns 170a (direction X) for weaving of the top tubular body portion such as top tubular body portion 117a of graft 100, the bottom warp yarns 160b are not lifted to prevent top fill yarns 170a from interweaving with bottom warp yarns 160b. Likewise, during passage of bottom fill yarns 170b (direction Y) for weaving of the bottom tubular body portion such as the bottom tubular body portion 117b of graft 100, the top warp yarns 160a are always lifted such that bottom fill yarns 170b are not interwoven with top warp yarns 160a. The plain tubular weave pattern as just described can be used to form straight portions of the inventive grafts which have a constant diameter. This pattern is then modified by gradually engaging or disengaging warp yarns to create tapers and/or shapes.

Figure 12:
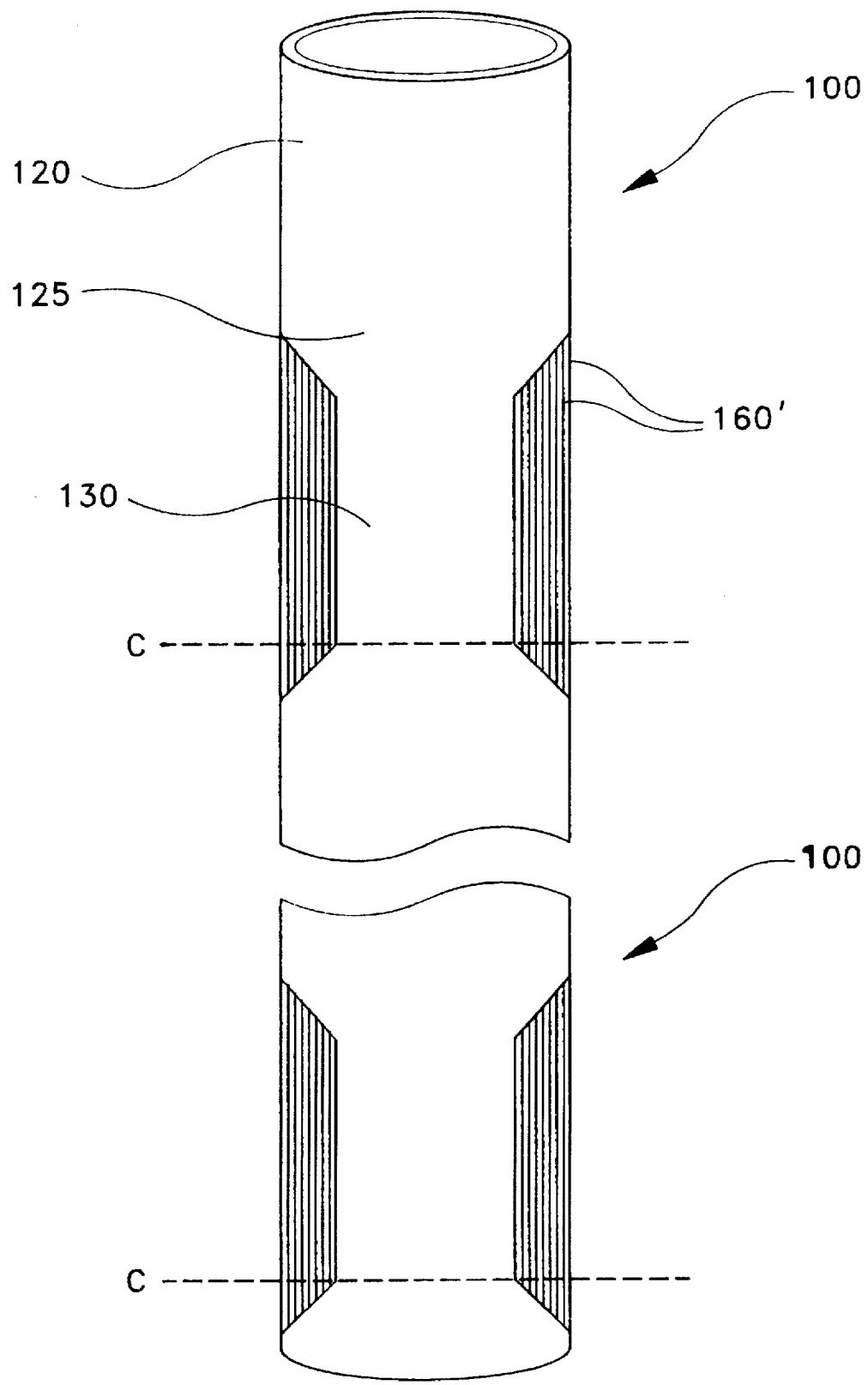
FIG. 12 is a perspective view of grafts being continuously flat-woven in accordance with the present invention, showing warp yarns gradually disengaged from the weave during weaving of one of the graft sections.

For example, the plain weave pattern shown in FIG. 11a and described above is formed by continuously passing top and bottom fill yarns 170a and 170b back and forth across warp yarns 160 to form first woven portion 120 of graft 100 shown in FIG. 12.

Figure 11B:
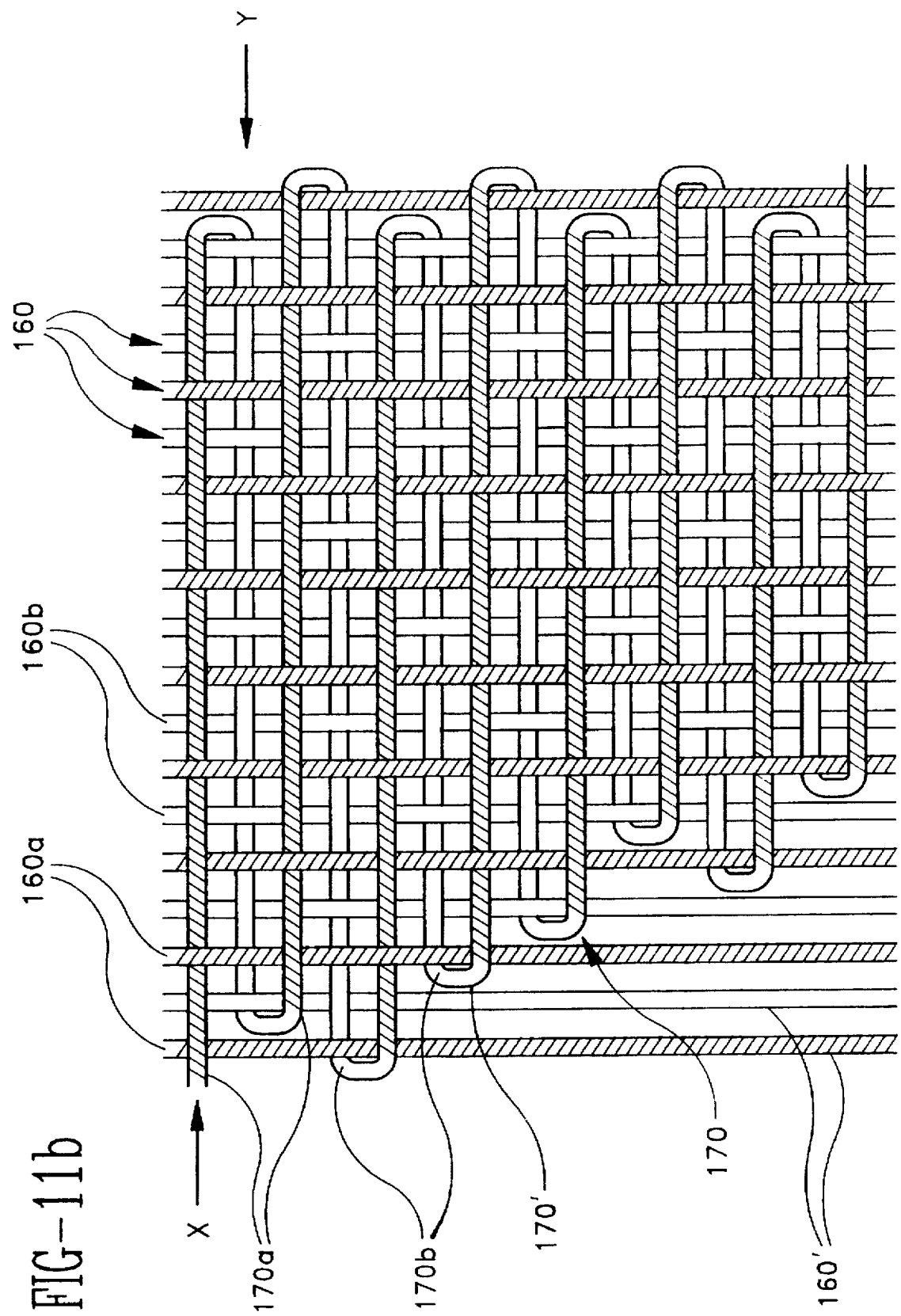

FIG. 11b shows a plain tubular weave pattern having a gradual disengaging of warp yarns. As seen in FIG. 11b, warp yarns 160' have been disengaged from the pattern and are no longer interwoven beginning at the fill yarn 170'. Likewise, the next set of picks shows an additional warp yarn being disengaged. As noted, the pattern is within the maximum disengagement of three warp yarns per four machine picks.

The disengaging of the warp yarns is accomplished by dropping the desired warp yarns from the end of the tubular flat-woven graft during the weaving process, such that the fill yarns are not interwoven across the warp yarns for that section of the pattern. Such dropping of warp yarns in a gradual manner forms the transitional portion of the graft. In continuous flat-weaving processes, the warp yarns are then re-engaged during the weave pattern once the transitional section has been completed.

Once the complete graft has been woven, the weave pattern may be repeated creating the next graft to be woven in a continuous process.

FIG. 12 shows a plurality of grafts 100 being woven in a continuous flat-weaving process, in accordance with the present invention. First woven portion 120 is of one inner diameter, for instance 24 millimeters, while second woven portion 130 is of another inner diameter different than that of first woven portion 120, for instance 18 millimeters. As such, first woven portion 120 requires more warp yarns 160 for weaving than does second woven portion 130. Thus, at transitional portion 125, the warp yarns are gradually disengaged from the weave, as depicted by disengaged warp yarns 160'. Since the grafts of the present invention are preferably fabricated using a continuous flat-weaving process, disengaged warp yarns 160' must be re-engaged into the weave pattern after completion of the second woven portion in order to begin weaving the first woven portion of the subsequent graft to be produced. Through such a continuous flat-weaving process, a plurality of grafts 100 can be woven in a continuous manner, and can be cut apart along line C after fabrication. Furthermore, disengaged warp yarns 160' are removed subsequent to weaving.

Figure 13:
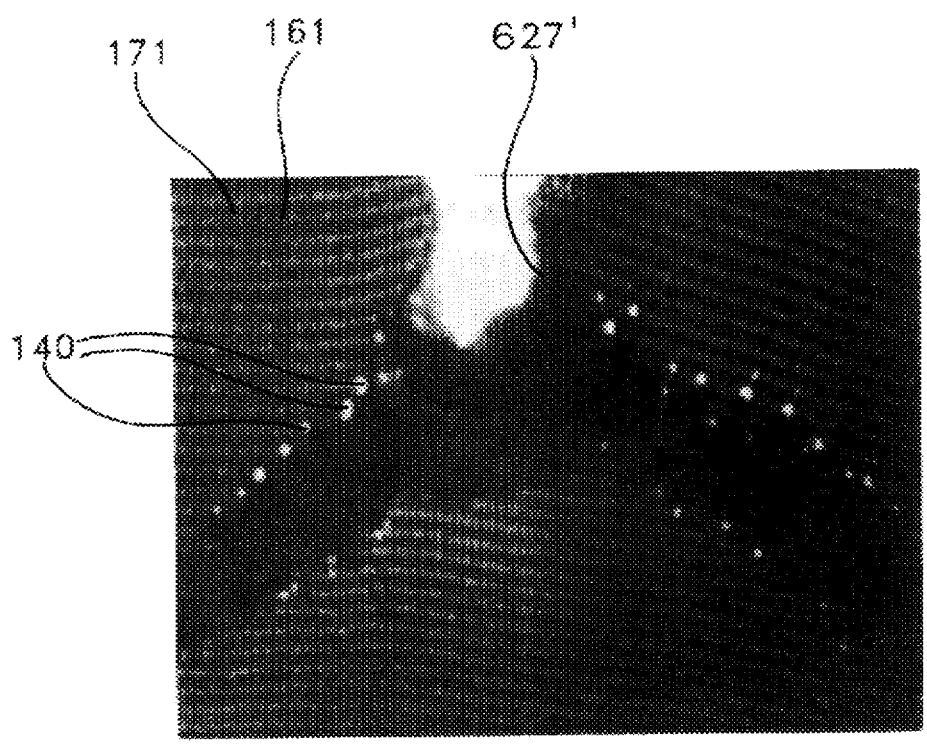
FIG. 13 shows a photomicrograph of the internal woven portion of a crotch section of a bifurcated graft of the prior art at a magnification of 10×.

For flat-weaving of bifurcated tubular grafts, prior art processes typically involved splitting of the warp yarns in half at the portion of the weave pattern where the graft splits from the aortic graft portion to the iliac leg portions, with the iliac leg sections of the graft therefore being woven with half the number of warp yarns as the aortic section of the graft. With such techniques, however, variations in the diameters of the iliac leg sections could not be accomplished in a seamless manner. Typically, when a tubular woven bifurcated graft with two different diameter iliac leg portions was required, i.e., when a tubular woven bifurcated graft having iliac leg portions with diameters different than that which would be formed by splitting the number of warp yarns in half was desired, the bifurcated graft would have to be first woven in a conventional manner, followed by cutting and suturing of the iliac to achieve the desired diameter. As discussed above, grafts produced in such a manner resulted in many drawbacks. For instance, the suture seam added to the wall thickness of the graft and added a discontinuity to the internal wall surface of the graft. Further, grafts requiring such post-fabrication suturing resulted in voids in the graft wall from the needle which was used for suturing. FIG. 13 shows a photomicrograph of an enlarged view of the internal portion of a prior art bifurcated graft woven of warp yarns 161 and fill yarns 171 at the crotch area 627' of the graft, where the two iliac leg portions branch off from the aortic portion. Needle holes 140 are present in the wall of the graft, representing holes through the graft wall which were made by a needle during suturing of the iliac leg portions to the aortic portion.

Figure 14:
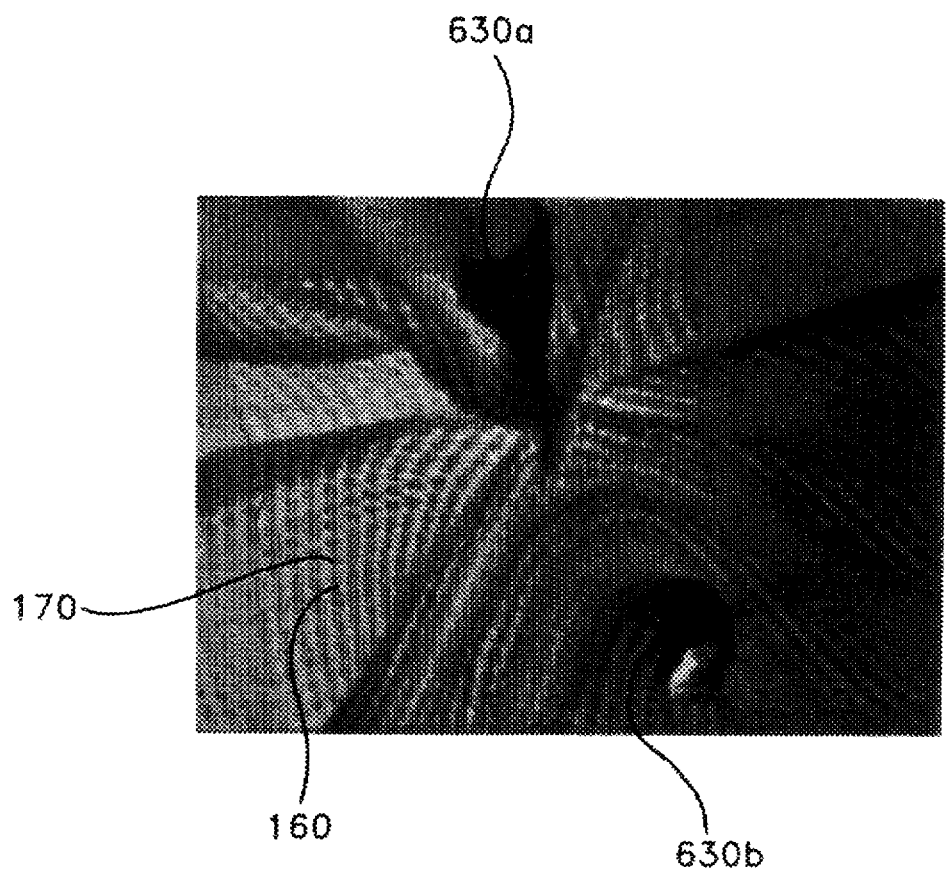
FIG. 14 shows a photomicrograph of the internal portion of a crotch section of a bifurcated graft made in accordance with the present invention at a magnification of 10×.

Through the present invention, split grafts such as bifurcated grafts can be flat-woven in a tubular form with varying diameters in the iliac portions and the aortic portion, without the need for such post-fabrication suturing. This is accomplished by a gradual transition in the number of warp yarns in the weave of the graft, as accomplished in the tapered grafts discussed above. Such gradual transition is accomplished by gradually engaging or disengaging warp yarns during the fabrication of the graft at the transition from the aortic graft portion to the iliac leg portions of the graft. A bifurcated graft produced in this manner is shown in an enlarged view at FIG. 14. FIG. 14 shows a bifurcated graft having first and second iliac woven portions 630a and 630b. As compared with the prior art graft shown in FIG. 13, the needle holes 140 which were created from the suturing needle required for attachment of the iliac legs in the prior art grafts are not present in the graft produced in accordance with the present invention.

Figure 17:
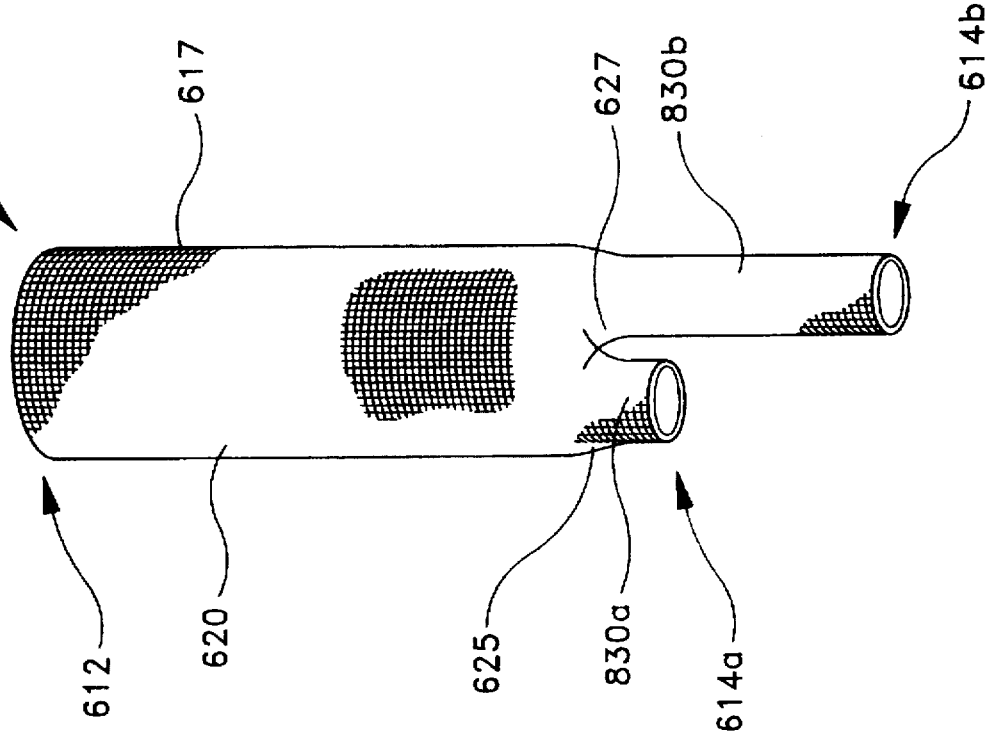

Referring generally to FIG. 15, a typical tubular woven bifurcated graft 600 includes a generally tubular body 617 having a first end 612 and opposed second ends 614a and 614b, defining therebetween an inner lumen 618 which permits passage of blood once bifurcated graft 600 is implanted in a blood vessel. Bifurcated graft 600 includes aortic woven portion 620 having a first inner diameter, and further includes first and second iliac woven tubular wall portions 630a and 630b each having an inner diameter which is different than the inner diameter of aortic woven portion 620. The inner diameters of first and second iliac woven portions 630a and 630b can be the same, as depicted in FIG. 15, or can be different, as depicted in 730a and 730b of FIG. 16. Further, iliac woven portions 630a and 630b can be of the same general length as shown in FIGS. 15 and 16, or can be of different general lengths, as shown at 830a and 830b in FIG. 17. Bifurcated graft 600 further includes bifurcated transitional woven portion 625 contiguous with aortic woven portion 620 and first and second iliac woven portions 630a and 630b at crotch 627 forming a bifurcated arch. Bifurcated transitional woven portion 625 forms a gradual taper such that bifurcated graft 600 gradually tapers from the inner diameter of aortic woven portion 620 to the inner diameters of first and second iliac woven portions 630a and 630b along the length of bifurcated transitional woven portion 625. The gradual tapering of bifurcated transitional woven portion 625 is accomplished by gradually disengaging and/or engaging a selected number of warp yarns from the weaving pattern during weaving of the graft, as accomplished in the preferred embodiment discussed above.

Figure 18:
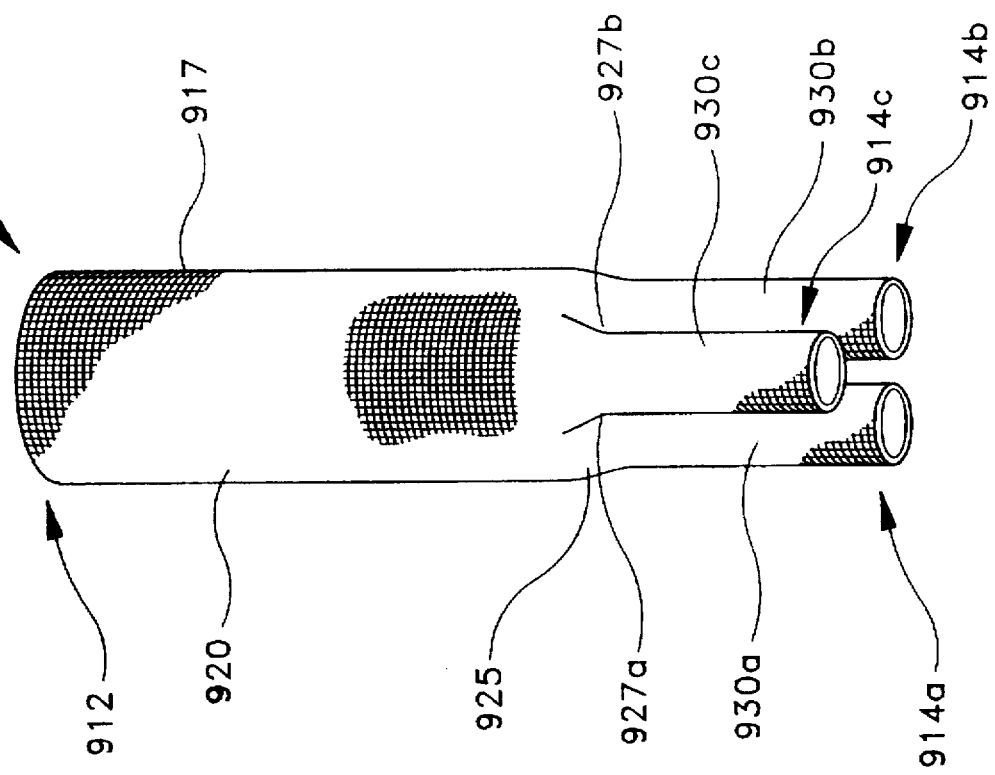
FIG. 18 depicts a perspective view of a trifurcated graft constructed in accordance with an alternative embodiment of the present invention.

FIG. 18 depicts a trifurcated graft 900 in accordance with an alternative embodiment of the present invention. Trifurcated graft 900 is of the same general configuration as bifurcated graft 600 shown in FIG. 17, including a generally tubular body 917 having first end 912, second ends 914a, 914b and 914c with first woven portion 920, transitional woven portion 925, first and second iliac woven portions 930a and 930b, and further includes an additional iliac leg as iliac woven portion 930c. Further, trifurcated graft 900 also includes crotches 927a, 927b and 927c (not shown), extending between transitional woven portion 925 and each of iliac woven portions 930a, 930b and 930c.

Figure 19:
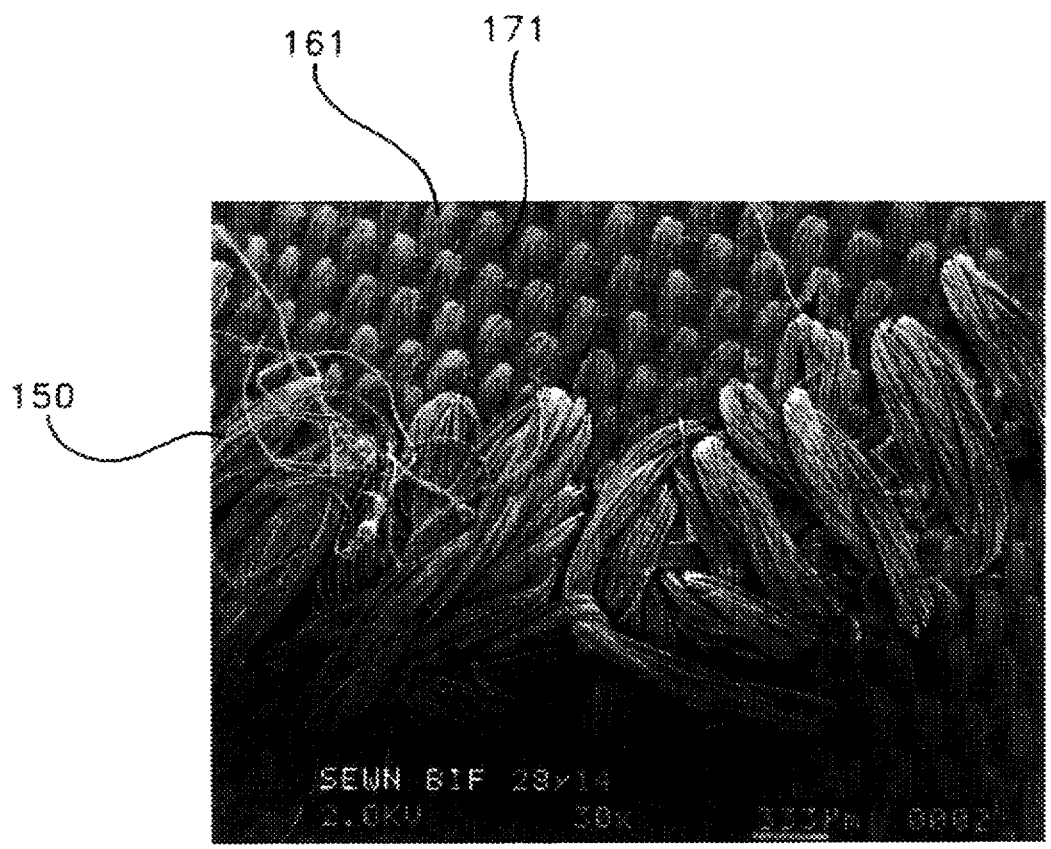
FIG. 19 shows a scanning electron micrograph of the internal portion of a crotch section of a bifurcated graft of the prior art at a magnification of 30×.

Prior art processes for tubular weaving of split grafts such as bifurcated and trifurcated grafts and the like resulted in holes or voids in the crotch area of the grafts, which in certain applications further resulted in undesirable porosity for the graft. The porosity of grafts is of vital importance, since such grafts are to be implanted into the body as fluid conduits and therefore must be of a porosity which prevents undesirable fluid leakage through the wall of the graft. The voids which were formed in the crotch area of bifurcated grafts produced by the prior art tubular weaving techniques resulted in high porosity of the graft at the crotch area and required suturing before they were acceptable for implantation. A bifurcated graft woven of warp yarns 161 and fill yarns 171 having such reinforcement sutures is depicted in FIG. 19, representing the prior art. FIG. 19 is a scanning electron micrograph of a prior art bifurcated graft showing the crotch area in an enlarged view. Warp yarns 161 and fill yarns 171 are seen generally in the micrograph. Crotch sutures 150 are shown, which undesirably create an added area of wall thickness in the graft.

Figure 20:
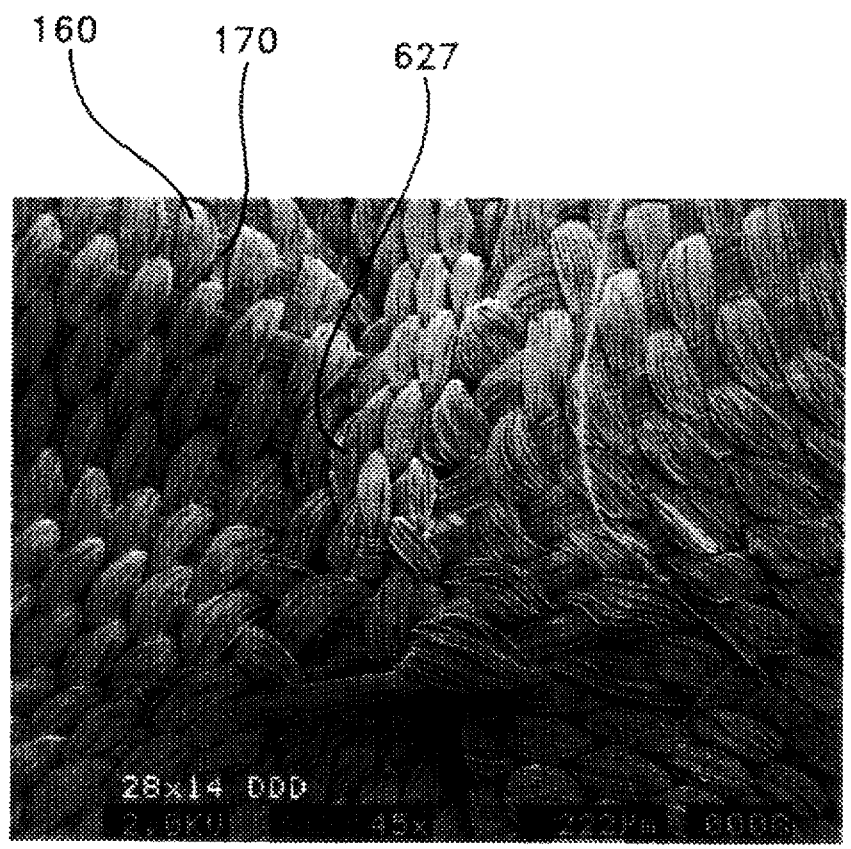
FIG. 20 shows a scanning electron micrograph of the internal portion of the crotch section of a bifurcated graft made in accordance with the present invention at a magnification of 45×.

The present inventor has discovered that such voids in the crotch area of a split graft can be avoided by gradually transferring the warp yarns during the weaving process from one woven section to another woven section contiguous thereto, thereby avoiding the necessity for post-fabrication suturing of voids. Thus, as depicted in FIG. 20, a closed weave is established in crotch 627 of a bifurcated graft 600, by gradually transferring the warp yarns during the weaving process from one woven section to another woven section contiguous therewith.

For example, during weaving of the bifurcated graft 600, as shown in FIG. 15, the warp yarns 160 which are being interwoven by the fill yarns 170 are gradually transferred from the aortic woven section 620 and the transitional woven section 625 to each of the iliac woven portions 630a and 630b.

Further, during weaving of bifurcated graft 600, two separate filling yarn shuttles (not shown) are required for weaving of the two distinct iliac woven portions 630a and 630b. To form the gradual transition in the crotch 627 avoiding holes, the shuttle designated for weaving of iliac woven portion 630a selectively and gradually engages warp yarns designated for weaving of iliac woven portion 630b. Likewise, the shuttle designated for weaving iliac woven portion 630b selectively and gradually engages warp yarns designated for weaving of iliac woven portion 630a. In this manner, the crotch 627 is woven using a simultaneous tapering effect at the interface between the aortic woven portion 620 and iliac woven portions 630a and 630b. As such, a smooth contiguous surface transition is obtained.

When weaving materials for implantation such as vascular grafts, however, it is necessary to provide exact inner diameters for the woven grafts. It has been discovered that, when using heat setting yarns such as polyester for the weaving yarns, the actual diameter after heat setting of the yarns is not easily predictable using conventional techniques. For example, in the prior art weaving of a tubular bifurcated graft having an aortic graft section of 26 millimeter inner diameter and two iliac leg sections of 13 millimeter inner diameter, the warp yarns were split in half in order to weave the iliac leg sections, with 627 warp yarns required for weaving of the aortic graft section, and 313 warp yarns (half of 627) being used for weaving of each of the iliac leg sections. When such a graft was flat-woven of polyester in tubular form and then heat set, however, the exact diameters of 26 millimeters for the aortic section and 13 millimeters for each of the iliac leg sections was not accomplished. Although the aortic section achieved the 26 millimeter diameter, the iliac leg portions shrunk to a smaller diameter than 13 millimeters, making the graft difficult to remove from the mandrel. Thus, the graft was not a true 26×13×13 set of diameters.

As noted above, the invention employs customized, programmable electronic jacquard weaving machines to gradually engage and/or disengage selected warp yarns from the weaving pattern during weaving of a flat-woven tubular product. With such capabilities, the present inventor has discovered that the number of warp yarns required for each of the tubular segments having different diameters can be pre-determined to account for the variation in heat shrinkage from one diameter to the next. Thus, in yet another alternate embodiment of the present invention, a method of forming a flat-woven synthetic tubular implantable prosthesis having a precise pre-determined internal diameter is provided. In the method, a desired weaving pattern is first selected for constructing the prosthesis. Preferably, the weaving pattern is selected from the group consisting of a simple weave (plain weave), a basket weave, a twill weave, and velour weaves. A desired yarn size and yarn diameter is then provided for the weaving pattern. The density at which the yarn is to be woven in the weave is then chosen, represented by a specific number of warp yarns per unit diameter. Additionally, a selected number of warp yarns is provided for weaving a suitable tubing edge. The desired internal diameter of the tubular prosthesis is then selected. Based upon knowing these parameters, the total number of warp yarns required to weave the tubular prosthesis with such a desired internal diameter can be calculated using the following formula:

$$N=S+(D\times\rho)$$

wherein N represents the total number of warp yarns required, S represents the number of edge warp yarns required to weave a suitable tubing edge, D represents the desired internal diameter and $\rho$ represents the number of warp yarns per unit of diameter. By applying the aforementioned steps, it has been discovered that an exact inner diameter for a given synthetic tubular woven product can be predetermined to account for variation in shrinkage due to heat setting. In a preferred embodiment, S is 29 when the diameter D is an even number, and S is 28 when the diameter is an odd number. In such a preferred embodiment, the density $\rho$ is 23 using a 1 ply/50 denier/48 filament polyester yarn.

Turning now to FIGS. 21–23, bifurcated graft 600 of FIG. 21 is depicted in a generally flat tubular shape subsequent to weaving, with top tubular wall portion 617a and bottom tubular wall portion 617b connecting at tubular edges 617c in a similar means as graft 100, previously discussed with relation to FIGS. 8–10.

Figure 25:
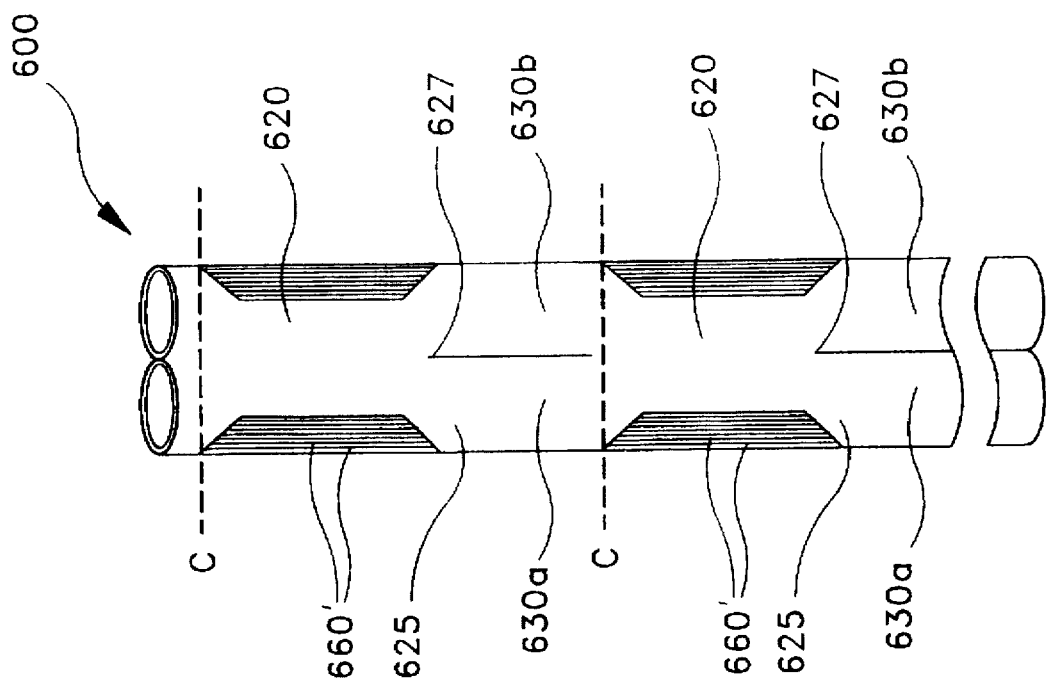
FIG. 25 is a perspective view of bifurcated grafts being continuously seamlessly flat-woven in accordance with the present invention, showing warp yarns gradually disengaged from the weave during weaving of the aortic section.
Figure 24:
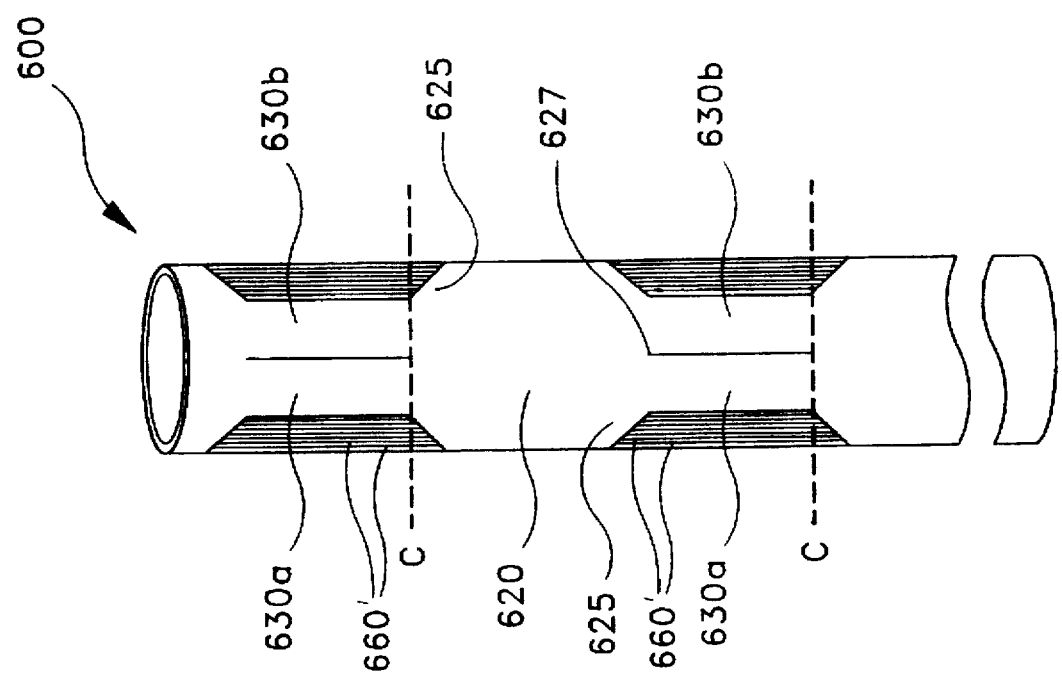
FIG. 24 is a perspective view of bifurcated grafts being continuously seamlessly flat-woven in accordance with the present invention, showing warp yarns gradually disengaged from the weave during weaving of the iliac sections.

Further, FIGS. 24 and 25 show a plurality of bifurcated grafts 600 being woven in a continuous flat-weaving process, in accordance with one embodiment of the present invention. Bifurcated grafts 600, as shown in FIGS. 24 and 25, are woven in a similar manner as grafts 100, depicted in FIG. 12. In FIG. 24, however, bifurcated graft 600 includes aortic woven portion 620 and first and second iliac woven portions 630a and 630b, with aortic woven portion 620 requiring more warp yarns for weaving than the iliac woven portions 630a and 630b. As such, during weaving of the iliac woven portions 630a and 630b, selected warp yarns are gradually disengaged from the weave at transitional woven portion 625 as represented by disengaged warp yarns 660'. In FIG. 25, iliac woven portions 630a and 630b require more warp yarns for weaving than aortic woven portion 620, and thus the disengaged warp yarns 660' are disengaged during weaving of the aortic woven section.

The tubular prostheses formed in accordance with the present invention can be used in surgical procedures as well as non-invasive procedures. Alternatively, the tubular prostheses of the present invention can be used in conjunction with a variety of stents in order to maintain the prostheses within the lumen of the body to be repaired. For example, FIG. 26 shows a bifurcated graft in accordance with one embodiment of the present invention, including a stent 50 affixed thereto at one portion of bifurcated graft 600. FIG. 27 shows a bifurcated graft in accordance with an alternative embodiment of the present invention, having stent 50 substantially along the entire length of tubular wall 617, positioned within the inner lumen of bifurcated graft. Such a stent 50 is well known in the art, and can be constructed in any desired shape and of any material known in the art, for example, a shaped memory alloy, as disclosed in International Application No. PCT/US95/01466, incorporated herein by reference. It is contemplated by the present invention that stent 50, as well as other stent types, can be used in such a manner with any of the tubular woven grafts of the present invention.

EXAMPLES

Unless otherwise noted, the grafts of all of the following examples were flat-woven in a tubular configuration using an electronic jacquard weaving machine. All of the grafts were flat-woven using a plain tubular weave pattern. The warp yarns and the fill yarns were constructed of single ply, 50 denier, 48 filament polyester with 170–190 warp ends per inch per layer and 86–90 fill yarns per inch per layer.

Example 1

The purpose of Examples 1 and 2 are to demonstrate that even when the electronic jacquard loom is used, unless the gradual engagement or disengagement of warp yarns is employed in accordance with the present invention, acceptable void free grafts will not be obtained.

A stepped graft (no taper) was flat-woven on an electronic jacquard loom in a tubular configuration to produce a 12 millimeter inner diameter section of the graft and a 10 millimeter inner diameter portion of the graft. The number of warp yarns required for weaving the 12 millimeter inner diameter portion of the graft was calculated using the above-mentioned method for pre-determining the number of warp yarns required to achieve the true desired diameters upon heat shrinking as follows:

$N=S+(D\times\rho)$ $N=29+(12\times23)$ $N=305$

The number of warp yarns required for weaving the 10 millimeter inner diameter portion of the graft was similarly calculated as follows:

$N=29+(10\times23)$ $N=259$

The 12 millimeter inner diameter portion of the graft was first flat-woven to a desired length. During the flat-weaving process, 46 warp yarns were disengaged from the weaving pattern all at once, i.e., at a single machine pick, in order to produce the 10 millimeter inner diameter portion of the graft. The graft thus produced included a 12 millimeter inner diameter portion and a 10 millimeter inner diameter portion. The transition between the two portions, however, included large holes between the weave sections of the graft which were visible to the naked eye.

Example 2

A graft having a 12 millimeter inner diameter portion and a 10 millimeter inner diameter portion was flat-woven in a manner similar to that of Example 1. During the transition from the 12 millimeter inner diameter portion to the 10 millimeter inner diameter portion, however, all 46 warp yarns were not disengaged at once transitioning to the 10 millimeter diameter portion. Instead, 4 or more warp yarns were disengaged for every 2 machine picks. The graft thus produced included a 12 millimeter inner diameter portion and a 10 millimeter inner diameter portion. The transition between the two portions, however, also included unacceptable holes between the weave sections of the graft which were visible to the naked eye.

Example 3

This example demonstrates the requirement for a maximum of three warp yarns which can be engaged or disengaged for every 4 machine picks. A graft having a 12 millimeter inner diameter portion and a 10 millimeter inner diameter portion was flat-woven in a manner similar to that of Example 2. During the transition from the 12 millimeter inner diameter portion to the 10 millimeter inner diameter portion, either 1 or 2 warp yarns were disengaged for every 4 machine picks, with a maximum of 3 warp yarns being disengaged for every 4 machine picks. The graft thus produced included a 12 millimeter inner diameter portion and a 10 millimeter inner diameter portion. The transition between the two portions included a gradual transition with no holes between the weave sections of the graft.

Example 4

This example demonstrates than the selection of the number of warp yarns for each desired diameter of a bifurcated graft must be made using the inventive method steps in order to obtain the true desired diameters and account for variation in heat shrinkage. A set of bifurcated grafts were flat-woven in a tubular configuration to produce an aortic section having a 24, 26 and 28 millimeter inner diameter and two iliac leg sections having a 12, 13 and 14 millimeter inner diameter for each leg section, respectively. The aortic section of the grafts were first flat-woven. When the weave reached the bifurcation portion, the previously described inventive method of gradually changing the warps was not employed. Instead, the number of warp yarns were split all at once, i.e., at a given pick, with one warp yarn being disengaged as necessary for one leg of the iliac leg section in order to produce the correct weave pattern (obtain an odd warp yarn number). The number of warp yarns used for each graft is shown in Tables 1–3.

None of the number of warp yarns for the aortic or the iliac sections were determined using the aforementioned inventive method, and as such, none of the warp yarn numbers were calculated in accordance with the formula stated therein.

TABLE 1

|  | NUMBER OF WARP YARNS USED FOR 24 mm AORTIC SECTION | NUMBER OF WARP YARNS USED FOR EACH 12 mm ILIAC SECTION |
| --- | --- | --- |
| Graft 1A | 583 | 291 |
| Graft 1B | 587 | 293 |
| Graft 1C | 591 | 295 |
| Graft 1D | 595 | 297 |

TABLE 2

|  | NUMBER OF WARP YARNS USED FOR 26 mm AORTIC SECTION | NUMBER OF WARP YARNS USED FOR EACH 13 mm ILIAC SECTION |
| --- | --- | --- |
| Graft 2A | 657 | 313 |
| Graft 2B | 631 | 315 |
| Graft 2C | 635 | 317 |
| Graft 2D | 639 | 319 |

TABLE 3

|  | NUMBER OF WARP YARNS USED FOR 28 mm AORTIC SECTION | NUMBER OF WARP YARNS USED FOR EACH 14 mm ILIAC SECTION |
| --- | --- | --- |
| Graft 3A | 675 | 337 |
| Graft 3B | 679 | 339 |
| Graft 3C | 683 | 341 |
| Graft 3D | 687 | 343 |

After the grafts were woven, they were placed on steel mandrels and heat set in an oven for a sufficient time and temperature to heat-set their shapes and size, i.e., at a temperature of 190°–200° C. for 14–16 minutes. After removing the grafts from the mandrels, the aortic section of each of the grafts was properly heat set to an inner diameter of 24, 26 and 28 millimeters. The iliac leg sections, however, were heat set too tightly on the mandrels, making it difficult to remove the leg sections from the mandrels. The actual inner diameter of each of the iliac leg sections was less than the desired 12, 13 and 14 millimeters, respectively.

Example 5

The following example demonstrates the use of the inventive method of forming a bifurcated graft of a desired diameter. This invention also shows, however, that when the rate of changing (disengaging or engaging) the warp yarns is greater than 3 warp yarns per 4 machine, unacceptable voids are present in the weave.

A set of bifurcated grafts were flat-woven in a tubular configuration in a similar manner as in Example 4, to produce an aortic section having a 24, 26 and 28 millimeter inner diameter and two iliac leg sections having a 12, 13 and 14 millimeter inner diameter for each leg section, respectively. The aortic section of the graft were first flat-woven. When the flat-woven. When the weave reached the bifurcation portion, the number of wrap yarns was adjusted by disengaging warp yarns from the weave pattern at a rate of 4 warp yarns being disengaged for every 4 machine picks.

The total number of warp yarns used for each graft was calculated by the formula as described herein.

$$N = S + (D \times p)$$

The calculated warp yarn numbers for each diameter section is set forth in the tables below.

TABLE 4

| NUMBER OF WARP YARNS USED FOR 24 mm AORTIC SECTION | NUMBER OF WARP YARNS USED FOR EACH 12 mm ILIAC SECTION |
| --- | --- |
| Graft 4 | 581 | 305 |

TABLE 5

| NUMBER OF WARP YARNS USED FOR 26 mm AORTIC SECTION | NUMBER OF WARP YARNS USED FOR EACH 13 mm ILIAC SECTION |
| --- | --- |
| Graft 5 | 627 | 327 |

TABLE 6

| NUMBER OF WARP YARNS USED FOR 28 mm AORTIC SECTION | NUMBER OF WARP YARNS USED FOR EACH 14 mm ILIAC SECTION |
| --- | --- |
| Graft 6 | 673 | 351 |

After the grafts were woven, they were placed on steel mandrels and heat set in an oven at a temperature of 190°–200° C. for 14–16 minutes. After removing the grafts from the mandrels, the aortic section of each of the grafts was properly heat set to an inner diameter of 24, 26 and 28 millimeters, respectively. The iliac leg sections were also properly heat set to an inner diameter of 12, 13 and 14 millimeters, respectively. When the disengaged warp yarns were removed from the exterior portion of the aortic graft section, however, holes visible to the naked eye were present in the tubular wall of the graft at the transition between the aortic portion and the iliac leg portions.

Example 6

This example demonstrates the use of the inventive embodiment, i.e., using gradually disengaged warp yarns to transition from the aortic section to the iliac sections, and the use of the inventive method of calculating the number of warp yarns required for a given diameter.

A set of bifurcated grafts were flat-woven in a tubular configuration in the same manner as in Example 5, to produce an aortic section having a 24, 26 and 28 millimeter inner diameter and two iliac leg sections having a 12, 13 and 14 millimeter inner diameter for each leg section, respectively. When the weave reached the bifurcation portion, however, the number of warp yarns was adjusted by disengaging warp yarns from the weave pattern at a rate of no more than 3 warp yarns being disengaged for every 4 machine picks. After the grafts were woven, they were heat set in the same manner as in Example 5. After removing the grafts from the mandrels, the inner diameters of the aortic section of each of the grafts measured 24, 26 and 28 millimeters, respectively, and diameters of the iliac leg sections measured 12, 13 and 14 millimeters, respectively. The precise desired inner diameters were thus obtained using the inventive method of determining the proper number of warp yarns necessary to account for heat set shrinkage. Moreover, when the disengaged warp yarns were subsequently removed from the exterior portion of the aortic graft section, no holes were present in the tubular wall of the graft at the transition between the aortic portion and the iliac leg portions. This clearly demonstrates the necessity for the gradual change in warp yarns as claimed herein.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. A flat-woven implantable open-ended tubular prosthesis having a plurality of warp yarns and fill yarns, said tubular prosthesis comprising a first portion and a second portion spaced from said first portion which define therebetween a transition tubular wall extent, said first portion having a first diameter and said second portion having a second diameter different from said first diameter, said tubular prosthesis further including a weaving pattern along said transition tubular wall extent, said weaving pattern having a gradual change in the number of warp yarns to provide a seamless substantially fluid-tight transition between said first portion and said second portion.

2. The prosthesis of claim 1 further including a first tubular wall seamlessly contiguous with said first portion of said transition tubular wall extent, said first tubular wall having a constant diameter.

3. The prosthesis of claim 2 further including a second tubular wall seamlessly contiguous with said second portion of said transition tubular wall extent, said second tubular wall having a constant diameter.

4. The prosthesis of claim 1 wherein said transition tubular wall extent is generally frustoconical in shape.

5. The prosthesis of claim 1 wherein said transition tubular wall extent is generally "S" shaped.

6. The prosthesis of claim 1 wherein said gradual change in the number of warp yarns is defined by a change of no more than 3 of said warp yarns for every 2 of said tubular fill yarns to create a substantially fluid-tight wall.

7. The prosthesis of claim 1 wherein said warp yarns and fill yarns include materials selected from the group consisting of polyester, polypropylene, polyethylene, polyurethane, polytetrafluoroethylene and mixtures thereof.

8. The prosthesis of claim 2 further including a plurality of secondary tubular walls each seamlessly contiguously woven with said second portion of said transition tubular wall extent.

9. The prosthesis of claim 8 wherein said plurality of secondary tubular walls and said second portion of said transition tubular wall extent define a seamless crotch.

10. The prosthesis of claim 9 wherein said plurality of secondary tubular walls is a pair of secondary tubular walls defining a bifurcated structure.

11. The prosthesis of claim 10 wherein said bifurcated structure includes said pair of secondary tubular walls of different diameters.

12. The prosthesis of claim 10 wherein said bifurcated structure includes said pair of secondary tubular walls of equal diameter.

13. The prosthesis of claim 1 further including a stent affixed to said tubular prosthesis.

14. A flat-woven implantable tubular prosthesis comprising first and second open ends defining a substantially fluid-tight tubular wall therebetween, said tubular wall including a plurality of warp yarns and fill yarns, said tubular wall being defined by a first elongate woven section with a first selected number of warp yarns therealong to define a first tubular internal diameter, and a second transition elongate woven section seamlessly contiguous with said first woven section and having a weaving pattern incorporating a gradual change in the number of warp yarns therealong to define at least a second tubular internal diameter different from said first tubular internal diameter.

15. The prosthesis of claim 14 wherein said second woven section is inwardly tapered.

16. The prosthesis of claim 14 wherein said second woven section is outwardly flared.

17. The prosthesis of claim 14 further including a third elongate woven section seamlessly contiguous with said second woven section.

18. The prosthesis of claim 14 further including a pair of elongate tubular members seamlessly contiguous with said second section.

19. The prosthesis of claim 18 wherein said tubular members have equal diameters.

20. The prosthesis of claim 18 wherein said tubular members have different diameters.

21. The prosthesis of claim 18 wherein said pair of tubular members have different lengths.

22. A flat-woven tubular implantable prosthesis having a plurality of warp yarns and fill yarns, said tubular prosthesis comprising first and second open ends defining a substantially fluid-tight tubular wall therebetween, said tubular wall having a first woven extent with a first selected number of warp yarns therealong to define a first tubular portion having a constant internal diameter therealong;

a transitional second woven extent contiguous with said first woven extent with at least a second selected number of warp yarns therealong defining a gradual change in the number of warp yarns to define at least a second tubular internal diameter which is different from said first tubular internal diameter, said transitional second woven extent defining a weaving pattern incorporating a seamless and gradual transition therealong; and a third woven extent contiguous with said transitional second woven extent, said third woven extent having a third selected number of warp yarns which is different from said first and said at least second selected number of warp yarns, said third woven extent defining a third tubular portion having a constant internal diameter therealong which is different from said first tubular internal diameter and said at least second tubular internal diameter.

23. The prosthesis of claim 22 wherein said gradual transition is defined by a change of no more than 3 of said warp yarns for every 2 of said tubular fill yarns to create a substantially fluid-tight wall.

24. The prosthesis of claim 22 further including at least a fourth woven extent seamlessly contiguous with said transitional second woven extent, said fourth woven extent having a fourth selected number of warp yarns which is different from said first, said at least second, and said third selected number of warp yarns, said at least fourth woven extent defining at least a fourth tubular portion having a constant internal diameter therealong which is different from said first tubular internal diameter, said at least second tubular internal diameter and said third tubular internal diameter, wherein said third woven extent and said fourth woven extent comprise at least two tubular members forming a bifurcated arch.

25. The prosthesis of claim 24 wherein said bifurcated arch includes warp yarns from said transitional second woven extent gradually interwoven with warp yarns from each of said at least two tubular members.

26. A method of forming a seamless flat-woven implantable tubular prosthesis comprising the steps of:

weaving a substantially fluid-tight tubular wall having a transitional diameter along a longitudinal extent thereof, said weaving including gradually engaging or disengaging warp yarns with fill yarns along said extent to transition from a first diameter to a second diameter different from said first diameter.

27. The method of claim 26 wherein said weaving further includes forming a first elongate portion of uniform diameter contiguous with one end of said longitudinal extent.

28. The method of claim 27 wherein said weaving further includes forming a second elongate portion of uniform diameter contiguous with the other end of said longitudinal extent, said diameter of said first elongate portion being different from said diameter of said second elongate portion.

29. A method of making a seamless flat-woven implantable tubular prosthesis comprising:

weaving a first section of said prosthesis having a first diameter using a first selected number of warp yarns, and seamlessly transitioning to a second section of said prosthesis having a second diameter different from said first diameter by gradually engaging or disengaging warp yarns with fill yarns to form a substantially fluid-tight prosthesis.

30. The method of claim 29 whereby said transitioning occurs without creating voids between said weave sections greater than the diameter of three warp yarns to create a substantially fluid-tight prosthesis.

31. The prosthesis of claim 18, wherein said second section further includes a crotch section to provide for said tubular member being seamlessly contiguous with said second section.

32. The prosthesis of claim 14, wherein said gradual change in the number of warp yarns is defined by a change of no more than 3 of said warp yarns for every 2 of said tubular fill yarns to create a substantially fluid-tight wall.

33. The prosthesis of claim 27, wherein said gradual change in the number of warp yarns is defined by a change of no more than 3 of said warp yarns for every 2 of said tubular fill yarns.

* * * * *

UNITED STATES PATENT AND TRADEMARK OFFICE
CERTIFICATE OF CORRECTION

PATENT NO. : 5,800,514  
DATED : September 1, 1998  
INVENTOR(S) : Nuñez et al.

Page 1 of 3

It is certified that error appears in the above-indentified patent and that said Letters Patent is hereby corrected as shown below:

IN THE TITLE:

| | |
|---|---|
| On the title page, item [54] and column 1, lines 1-3, | now reads "SHAPED WOVEN TUBULAR SOFT-TISSUE PROSTHESES AND METHODS OF MANUFACTURING", should read --SHAPED WOVEN TUBULAR SOFT-TISSUE PROSTHESES AND METHODS OF MANUFACTURING THE SAME--; |
| Column 1, Line 67, | now reads "copending", should read --co-pending--; |
| Column 2, Line 8, | now reads "on e", should read --one--; |
| Column 2, Line 27, | now reads "yam", should read --yarn--; |
| Column 2, Line 33, | now reads "yam", should read --yarn--; |
| Column 3, Line 3, | now reads "manually cut an bifurcated graft", should read --manually cut and tailor one of the legs of a bifurcated graft--; |

UNITED STATES PATENT AND TRADEMARK OFFICE
CERTIFICATE OF CORRECTION

PATENT NO. : 5,800,514
DATED : September 1, 1998
INVENTOR(S) : Nuñez et al.

It is certified that error appears in the above-indentified patent and that said Letters Patent is hereby corrected as shown below:

| | |
|---|---|
| Column 4, Line 65, | now reads "predetermined", should read --pre-determined--; |
| Column 5, Line 1, | now reads "yam", should read --yarn--; |
| Column 7, Line 2, | now reads "yam", should read --yarn--; |
| Column 7, Line 9, | now reads "yam", should read --yarn--; |
| Column 10, Line 20, | now reads "yam", should read --yarn--; |
| Column 10, Line 23, | now reads "yam", should read --yarn--; |
| Column 10, Line 24, | now reads "yam", should read --yarn--; |

UNITED STATES PATENT AND TRADEMARK OFFICE
CERTIFICATE OF CORRECTION

PATENT NO. : 5,800,514
DATED : September 1, 1998
INVENTOR(S) : Nuñez et al.

It is certified that error appears in the above-indentified patent and that said Letters Patent is hereby corrected as shown below:

Column 10, Line 25,      now reads "yam", should read --yarn--;

Column 11, Line 10,      now reads "yam", should read --yarn--;

Column 11, Line 50,      now reads "yam", should read --yarn--;

Column 12, Line 13,      now reads "yam". should read --yarn--;

Column 18, Line 64,      delete "When the flat-woven".

Signed and Sealed this

Sixteenth Day of February, 1999

Attest:

*Attesting Officer*

*Acting Commissioner of Patents and Trademarks*